US007273618B2

(12) United States Patent
Frey, II et al.

(10) Patent No.: US 7,273,618 B2
(45) Date of Patent: Sep. 25, 2007

(54) METHOD FOR ADMINISTERING AGENTS TO THE CENTRAL NERVOUS SYSTEM

(75) Inventors: William H. Frey, II, White Bear Lake, MN (US); Robert Gary Thorne, Minneapolis, MN (US)

(73) Assignee: Chiron Corporation, Emeryville, CA (US)

( * ) Notice: Subject to any disclaimer, the term of this patent is extended or adjusted under 35 U.S.C. 154(b) by 331 days.

(21) Appl. No.: 10/301,185

(22) Filed: Nov. 21, 2002

(65) Prior Publication Data

US 2003/0072793 A1 Apr. 17, 2003

Related U.S. Application Data

(63) Continuation of application No. 09/458,562, filed on Dec. 9, 1999, now abandoned, which is a continuation-in-part of application No. 09/208,539, filed on Dec. 9, 1998, now abandoned.

(51) Int. Cl.
*A61K 9/70* (2006.01)
*A61K 9/14* (2006.01)

(52) U.S. Cl. ..................... 424/449; 424/489

(58) Field of Classification Search ............... 424/450, 424/427, 428, 434, 435, 43; 514/12, 21, 514/937
See application file for complete search history.

(56) References Cited

U.S. PATENT DOCUMENTS

| | | | |
|---|---|---|---|
| 4,376,110 A | 3/1983 | David et al. | |
| 4,464,358 A | 8/1984 | Cox | |
| 4,479,932 A | 10/1984 | Bodor | |
| 4,507,391 A | 3/1985 | Pukel et al. | |
| 4,579,858 A | 4/1986 | Fernö et al. | |
| 4,584,278 A | 4/1986 | Knauf | |
| 4,613,500 A | 9/1986 | Suzuki et al. | |
| 4,639,437 A | 1/1987 | della Valle et al. | |
| 4,666,829 A | 5/1987 | Glenner et al. | |
| 4,675,287 A | 6/1987 | Reisfeld et al. | |
| 4,746,508 A | 5/1988 | Carey et al. | |
| 4,801,575 A | 1/1989 | Pardridge | |
| 4,822,594 A | 4/1989 | Gibby | |
| 4,895,452 A | 1/1990 | Yiournas et al. | |
| 4,902,505 A | 2/1990 | Pardridge et al. | |
| 4,921,706 A | 5/1990 | Roberts et al. | |
| 5,153,002 A | 10/1992 | McMullen | |
| 5,250,023 A * | 10/1993 | Lee et al. .................. 604/20 |
| 5,624,898 A | 4/1997 | Frey, II | |
| 5,985,320 A * | 11/1999 | Edwards et al. ............ 424/450 |
| 6,244,265 B1 * | 6/2001 | Cronk et al. ........... 128/200.24 |

FOREIGN PATENT DOCUMENTS

| EP | 0 145 209 | 6/1985 |
|---|---|---|
| EP | 0 333 574 | 9/1989 |
| EP | 0 351 808 | 1/1990 |
| EP | 0 539 087 | * 4/1993 |
| FR | 2 260 329 | 9/1975 |
| JP | 2-214 | 1/1990 |
| JP | 2-78632 | 3/1990 |
| JP | 7-41428 | 2/1995 |
| JP | 2590548 | 12/1996 |
| JP | 2734554 | 1/1998 |
| SU | 1139 444 | 2/1985 |
| WO | WO86/02271 A1 | 4/1986 |
| WO | WO86/04233 | 7/1986 |
| WO | WO88/09171 | 12/1988 |
| WO | WO89/01343 | 2/1989 |
| WO | WO97/49419 A1 | 12/1997 |
| WO | WO98/34645 A1 | 8/1998 |

OTHER PUBLICATIONS

Altman, J., *Nature*, 1989, vol. 337(688).
Amaducci, L., et al., "Use of Phosphatidylserine in Alzheimer's Disease," *Annals of New York Academy of Science*, 1991, pp. 245-249, vol. 640.
Ang et al., "Blood-Cerebrospinal Fluid Barrier to Arginine Vasopressin, Desmopressin and Desglycinamide Arginine-Vasopressin in the Dog," *Journal of Endocrinology*, 1982, pp. 319-325, vol. 93.
Aoki et al., "Distribution and Removal of Human Serum Albumin -Technetium 99m Instilled Intranasally," *British Journal of Clinical Pharmacology*, 1976, pp. 869-878, vol. 3.
Baker, H., et al., *Experimental Brain Research*, 1986, pp. 461-473, vol. 63.
Boies et al., *Fundamentals of Otolaryngology*, 1989, pp. 184-185.
Boissière, F., et al., "Decrease of TrkA Messenger RNA Content in Cholinergic Neurons of the Striatum and Basal Forebrain in Alzheimer's Disease," (date unknown), P03.041.
Bowen, D., et al., *The Lancet*, 1979, pp. 11-14.
Broadwell, "Transcytosis of Macromolecules Through the Blood-Brain Barrier: A Cell Biological Perspective and Critical Appraisal," *Acta Neuropathology*, 1989, pp. 117-128, vol. 79.
Chase, M., "Nerve- Growth Factors Brighten the Medical Horizon," *The Wall Street Journal*, Mar. 12, 1992, pp. B1 and B7.
Chen, X., et al., "Delivery of Nerve Growth Factor to the Brain Via the Olfactory Pathway," *Journal of Alzheimer's Disease*, 1998, pp. 35-44, vol. 1.
Chen, X., et al., "Olfactory Route: A New Pathway to Deliver Nerve Growth Factor to the Brain," *Neurobiology of Aging (Suppl. 4S)*, 1998, Abstract No. 1086.
Chia, L., et al., *Biochimica et Biophysica Acta*, 1984, pp. 308-312, vol. 775.

(Continued)

*Primary Examiner*—Gollamudi S. Kishore
(74) *Attorney, Agent, or Firm*—Denise Bergin; Susan L. Abrahamson; Alisa A. Harbin

(57) ABSTRACT

The present invention is directed to a method for delivering agents to the central nervous system by way of a tissue innervated by the trigeminal nerve that is outside the nasal cavity. Such a method of delivery can be useful in the treatment of central nervous system and/or brain disorders.

7 Claims, No Drawings

OTHER PUBLICATIONS

Chien, et al., *Nasal Systemic Drug Delivery*, 1989, pp. 18-19, 44-49, 56-59, 82-85, 292-293.

Chien, et al., in *CRC Critical Reviews in Therapeutic Drug Carrier Systems*, 1987, pp. 67-194, vol. 4.

Chou, K., et al., "Distribution of Antihistamines into the CSF Following Intranasal Delivery", *Biopharmaceutics & Drug Disposition*, 1997, pp. 335-346, vol. 18(4), Abstract.

Chou, K., et al., "Lidocaine Distribution into the CNS Following Nasal and Arterial Delivery: A Comparison of Local Sampling and Microdialysis Techniques", *International Journal of Pharmaceutics*, 1998, pp. 53-61, vol. 171, Abstract.

Chou, K., et al., "The Distribution of Local Anesthetics into the CSF Following Intranasal Administration," *International Journal of Pharmaceutics*, 1998, pp. 137-145, vol. 168.

Clements, J., et al., "Alzheimer Disease and Associated Disorders," 1990, pp. 35, 37, 39, 41, vol. 4(1).

Clements, J., et al., "Ganglioside Alterations in Alzheimer's Disease and Treatment of Alzheimer's Disease with GM-I," *AHAF Alzheimer's Disease Research Conference*, Feb. 17, 1989 (Abstract), 1 pg.

Crook, T., et al., *Psychopharmacology Bulletin*, 1992, pp. 61-66, vol. 28(1).

Cummings, J., et al., "Dementia of the Alzheimer Type," *JAGS*, 1986, pp. 12-19, vol. 34.

DeMyer, W., "Brainstem and Cranial Nerves," *Neuroanatomy*, 1988, pp. 164-1669, John Wiley and Sons, New York.

Dodd and Kelly, "The Brain Stem and Reticular Core," *Trigeminal System*, pp. 701-710.

Doty, R.L., *Annals of National Academy of Sciences*, 1989, pp. 76-86, vol. 561.

Draghia, R., "Gene Delivery into the Central Nervous System by Nasal Instillation in Rats," *Gene Therapy*, 1995, pp. 418-423, vol. 2(6).

Editors, *Neurobiology of Aging*, 1986, vol. 7(599).

Eisenbarth et al., "Monoclonal Antibody to a Plasma Membrane Antigen of Neurons," *Proceedings of the National Academy of Sciences USA*, 1979, pp. 4913-4917, vol. 76.

Emory et al., "Ganglioside Monoclonal Antibody (A2B5) Neurofibrillary Tangles," *Fed. Proceedings*, 1986, p. 1728, vol. 45.

Emory et al., "Ganglioside Monoclonal Antibody (A2B5) Neurofibrillary Tangles," *Neurology*, 1987, pp. 768-772, vol. 37.

Eppstein et al., "Alternative Delivery Systems for Peptides and Proteins as Drugs," *CRC Critical Reviews in Therapeutic Drug Carrier Systems*, 1988, pp. 99-139, vol. 5.

Fabian et al., "Intraneuronal IgG in the Central Nervous System: Uptake by Retrograde Axonal Transport," *Neurology*, 1987, pp. 1780-1784.

Fabian, R., *Neurology*, 1990, pp. 419-422, vol. 40.

Ferreyra-Moyano, H., *International Journal of Neuroscience*, 1989, pp. 157-197, vol. 49.

Fischer, W., et al., *Nature*, Sep. 3, 1987, pp. 65-68, vol. 329.

Fredman, P., et al., "Monoclonal Antibody A2B5 Reacts with Many Gangliosides in Neuronal Tissue," *Archives of Biochemistry and Biophysics*, 1984, pp. 661-666, vol. 233(2).

Frey II, W., et al., "Delivery of$^{125}$ I-NGF to the Brain Via the Olfactory Route," *Drug Delivery*, 1997, pp. 87-92, vol. 4.

Frey II, W., et al., "Research Advances in Alzheimer's Disease Research," *Progress in Clinical Neurosciences*, 1988, pp. 287-303, vol. 1.

Frey II, W., et al., "Research Advances in Alzheimer's Disease and Related Disorders," 1995, pp. 329-335.

Frey II, W., et al., "Alzheimer's Neurofibrillary Tangles Are Labeled by Ganglioside Monoclonal Antibody A2B5," *Alzhemier's Disease: Advance in Basic Research and Therapies*, 1987, pp. 411-415.

Friden, P., et al., *Science*, Jan. 15, 1993, pp. 373-377, vol. 259.

Galanos, et al., "Preparation and Properties of Antisera Against the Lipid-A Component of Bacterial Lipopolysaccharides," *European Journal of Biochemistry*, 1971, pp. 116-122, vol. 24.

Ghanbari, H., et al., *JAMA*, Jun. 6, 1990, pp. 2907-2910, vol. 263(21).

Gopinath, et al., "Target Site of Intranasally Sprayed Substances and Their Transport Across the Nasal Mucosa: A New Insight into the Intranasal Route of Drug-Delivery," *Current Therapeutic Research*, 1978, pp. 596-607, vol. 23.

Gorio, et al., *Neuroscience*, 1983, pp. 417-429, vol. 8.

Gray, H., "The Nervous System: The Cranial Nerve," *Gray's Anatomy*, 1977, pp. 725-738, Crown Publishers, Inc.

Graziadei et al., "Neurogenesis and Neuron Regeneration in the Olfactory System of Mammals. I. Morphological Aspects of Differentiation and Structural Organization of the Olfactory Sensory Neurons," *Journal of Neurocytology*, 1979, pp. 1-18, vol. 8.

Guthrie, K., et al., *The Journal of Comparative Neurology*, 1991, pp. 95-102, vol. 313.

Hahn, B., et al., "A Public Idiotypic Determinant Is Present on Spontaneous Cationic IgG Antibodies to DNA from Mice of UrRelated Lupus-Prone Strains I," *Chemical Abstracts*, 1985, vol. 102, Abstract No. 102:22541d.

Hammerschlag et al., "Axonal Transport and the Neuronal Cytoskeleton," *Basic Neurochemistry: Molecular, Cellular, and Medical Aspects*, 1989, pp. 457-478.

Hardy, J. G., et al., "Intranasal Drug Delivery by Spray and Drops," *Journal of Pharmacy and Pharmacology*, 1985, pp. 294-297, vol. 37.

Harris, A., *Delivery Systems for Peptide Drugs*, date illegible, pp. 191 and 194.

Hefti, F., et al., "Function of Neurotrophic Factors in the Adult and Aging Brain and Their Possible Use in the Treatment of Neurodegenerative Disease," *Neurobiology of Aging*, 1989, pp. 515-533, vol. 10.

Hefti, F., et al., "Protective Effects of Nerve Growth Factor and Brain-Derived Neurotrophic Factor on Basal Forebrain Cholinergic Neurons in Adult Rats with Partial Fimbrial Transections," *Progress in Brain Research*, 1993, pp. 257-263, vol. 98.

Hussain, M.A., et al., "Nasal Administration of a Cognition Enhancer Provides Improved Bioavailability but Not Enhanced Brain Delivery," *Journal of Pharmaceutical Sciences*, Sep. 1990, pp. 771-772, vol. 79(9).

Isenbach, et al., "Monoclonol Antibody to a Plasma Membrane Antigen of Neurons," *Proceedings of the National Academy of Sciences USA*, pp. 4913-4917, vol. 76.

Kare, M.R., et al., *Science*, 1969, pp. 952-953, vol. 163.

Kasai, et al., "The Monoclonal Antibody A2B5 Is Specific to Ganglioside $G_{Qlc}$," *Brain Research*, 1983, pp. 155-158, vol. 277.

Kato, et al., "Basic Fibroblast Growth Factor-Binding Sites in Alzheimer's Disease Brains," *Neurobiology of Aging*, 1990, vol. 11(268), Abstract #62.

Katzman, R., *The New England Journal of Medicine*, 1986, pp. 964-973.

Kern, W., et al., "Central Nervous System Effects Intranasally Administered Insulin During Euglycemia in Men", *Diabetes*, Mar. 1999, pp. 557-563, vol. 48.

King, M., *Atlanta Journal*, 1989 (Science/Medicine Section).

Knusel, B., et al., *The Journal of Neuroscience*, 1990, pp. 558-570, vol. 10(2).

Kristensson, K., et al., *Acta Neuropathology*, 1971, pp. 145-154, vol. 19.

Kumar, T.C., et al., Pharmacokinetics of Progesterone After its Administration to Ovariectomized Rhesus Monkeys by Injection, Infusion, or Nasal Spraying, *Proceedings of the National Academy of Sciences USA*, 1982, pp. 4185-4189, vol. 79.

Kumar, T.C., et al., "Neuroendocrine Regulation of Fertility Int. Symp. Simla. 1974," 1976, pp. 314-322.

Kumar, T.C., et al., *Current Science*, 1974, pp. 435-439, vol. 43.

Kumbale, R., "GM1 Delivery to the CSF Via the Olfactory Pathway," *Drug Delivery*, 1999, pp. 23-30, vol. 6.

Langer, L., et al., *Technology Review*, Feb.-Mar. 1991, 8 pgs, vol. 94(2).

Lapchak, P., et al., *Neuroreport*, 1992, pp. 405-408, vol. 3.

Lee et al., "Intranasal Delivery of Proteins and Peptides," *BioPharm*, Apr. 1988, pp. 30-37.

Mark, J., *Science*, 1990, pp. 984-985, vol. 249.

Mathison et al., "Nasal Route for Direct Delivery of Solutes to the Central Nervous System: Fact or Fiction?," *Journal of Drug Targeting*, 1998, pp. 415-441, vol. 5(6).

Okle, S., "Tracking Alzheimer's: Tangles in Brain Cells," *The Washington Post*, Feb. 25, 1991.

Olson, L., et al., *Journal of Neural Transmission*, 1992, pp. 79-95, vol. 4.

Pardridge, W.M., et al., "High Molecular Weight Alzheimer's Disease Amyloid Peptide Immunoreactivity in Human Serum and CSF Is an Immunoglobulin G," *Biochemical and Biophysical Research Communications*, 1987, Abstract.

Pearson, R.C.A., et al., *Proceedings of the National Academy of Sciences USA*, 1985, pp. 4531-4534, vol. 82.

Peele, D., et al., *Toxicology and Applied Pharmacology*, 1991, pp. 191-202, vol. 107.

Phelps, C.H., et al., *Neurobiology of Aging*, 1989, pp. 205-207, vol. 10.

Pitha et al., "Drug Solubizers to Aid Pharmacologists: Amorphous Cyclodextrin Derivatives," *Life Sciences*, 1988, pp. 493-502, vol. 43.

Rapport et al., "Present Status of the Immunology of Gangliosides," *Advances in Experimental Medicine and Biology*, 1984, pp. 15-25, vol. 174.

*Regeneron Annual Report*, 1991, 41 pgs.

Represa, A., et al., *Brain Research*, 1988, pp. 355-359, vol. 457.

Roberts, E., *Neurobiology of Aging*, 1986, pp. 561-567, vol. 7.

Ryan, C., *Focus On*, 1986, pp. 1-13, vol. 7, University of Cincinnati Medical Center.

Sakane, T., et al., *Journal of Pharmacy and Pharmacology*, 1991, pp. 449-451, vol. 43.

Schofield, P.R., *TINS*, 1988, pp. 471-472, vol. 11.

Seiler, M., et al., *Brain Research*, 1984, pp. 33-39, vol. 300.

Shipley, M.T. *Brain Research*, 1985, pp. 129-142, vol. 15.

Smith, A., et al., "Intranasally Administered Alpha/Beta Interferon Prevents Extension of Mouse Hepatitis Virus, Strain JHM, into the Brains of BALB/cByJ Mice," *Antiviral Research*, 1987, pp. 239-245, vol. 8(5)(6).

Snyder et al., "Molecular Mechanisms of Olfaction," *J Biol. Chem.*, 1988, pp. 13971-13974, vol. 263.

Stryer, *Biochemistry*, 1988, pp. 288-291.

Talamo, B.R., et al., *Nature*, 1989, pp. 736-739, vol. 337.

Templeton, F., "Regeneron Has Research on the Brain," *Business Week*, Jul. 27, 1992, 2 pgs.

Thorne, R., et al., "Delivery of Insulin-Like Growth Factor-1 (IGF-1) to the Brain Via the Olfactory Pathway: A Possible Therapeutic Strategy for Alzheimer's Disease (AD)," *Neurobiol. of Aging*, 1998, Abstract No. 1089, Suppl. 4S.

Thorne, R., et al., "Delivery of Insulin-Like Growth Factor-I (IGF-1) to the Brainstem and Cerebellum Following Intranasal Administration: A Noninvasive Drug Delivery Strategy for Bypassing the Blood-Brain Barrier," *Pharm. Sci.*, 1998, p. 555, vol. 1(1).

Tiemeyer, M., et al., *J. Biol. Chem.*, 1989, pp. 1671-1681, vol. 264.

Tuszynaki, M., et al., "PO3.33, Long-Term Basal Forebrain Cholinergic Rescue by Nerve Growth Factor Gene Therapy in Correlative Primate Models of Alzheimer's Disease," *Neurology*, 1996, vol. 46, 1 pg.

Wesbey, G., et al., *Physiological Chemistry & Physics & Medical NMR*, 1984, pp. 145-155, vol. 16(2), (Abstract-1 pg.).

Williams, R., et al., *Brain Research*, 1988, pp. 21-27, vol. 463.

Wolters, E., et al., "Double-Blind Placebo-Controlled DGAVP in Early Alzheimer's Disease Patients," *Neurobiology of Aging*, 1990, vol. 11:348 (Abstract No. 391).

Wolters, E., et al., *Neurology*, 1990, pp. 1099-1101, vol. 40.

Yoko, S., et al., "Glycolipids in the Brain of Alzheimer's Disease and Sulfate Ion in Serum of Demented Patients," *Biol. Abstr.*, 1985, vol. 79(2):AB-665, Ref. No. 15157; 1 pg.

Young, et al., "Production of Monoclonal Antibodies Specific for Two Distinct Steric Portions of the Glycolipid Ganglio-N Triosylceramide (Asialo $GM_2$)," *J. Exp. Med.*, 1979, pp. 1008-1019, vol. 150.

M.F. McCarty, "Enhancing Central and Peripheral Insulin Activity as a Strategy for the Treatment of Endogenous Depression—An Adjuvant Role for Chromium Picolinate," *Medical Hypotheses*, 1994, pp. 247-252, vol. 43.

Zakzewski, C.A., et al., "Transdermal Delivery of Regular Insulin to Chronic Diabetic Rats: Effect of Skin Preparation and Electrical Enhancement," *Journal of Controlled Release*, 1998, pp. 267-272, vol. 50.

Rote Liste 1997, Editio Cantor Verlag, Aulendorf, 1996, pp. 71140-71150.

\* cited by examiner

METHOD FOR ADMINISTERING AGENTS TO THE CENTRAL NERVOUS SYSTEM

CROSS REFERENCE TO RELATED APPLICATIONS

This application is a continuation of U.S. application Ser. No. 09/458,562, filed Dec. 9, 1999 now abandoned, which is a continuation-in-part of U.S. application Ser. No. 09/208,539, filed Dec. 9, 1998, now abandoned.

FIELD OF THE INVENTION

The present invention is directed to a method for delivering agents to the central nervous system by way of a tissue innervated by the trigeminal nerve that is outside the nasal cavity. Such a method of delivery can be useful in the treatment of central nervous system and/or brain disorders.

BACKGROUND OF THE INVENTION

The central nervous system (CNS) includes several tissues and organs, such as the brain, the brain stem, and the spinal cord. Each of these organs and tissues is made up of a variety of different types of cells and subcellular structures, e.g. neurons, glial cells, dendrites, axons, myelin, and various membranes. The CNS is isolated from the external world by several membranes that both cushion and protect these organs, tissues, cells, and structures. For example, the membranes that form the blood-brain barrier protect the brain from certain contents of the blood. The blood-cerebrospinal fluid barrier protects other portions of the CNS from many chemicals and microbes.

Access to the CNS for some substances is provided by specialized active transport systems or through passive diffusion through the protective membrane into the CNS. Present methods for delivering desired therapeutic agents to the CNS are typically invasive. For example, a pump implanted in the skull (an intracerebroventricular pump) can effectively deliver a variety of useful compounds to the brain. However, implanting such a pump requires brain surgery, which can entail a variety of serious complications. Certain compounds (e.g. epidural painkillers) can be injected directly through the protective membrane into the CNS. Such injection is, however, impractical for most medications.

Better methods for administering desired agents to the CNS, brain, and/or spinal cord are needed.

SUMMARY OF THE INVENTION

The present invention relates to a method for transporting or delivering an agent to a central nervous system of a subject. The method employs administration of the agent to a tissue outside the subject's nasal cavity and innervated by the trigeminal nerve. In one embodiment, the method administers the agent through the mucosa or epithelium of the tongue, mouth, skin, or conjunctiva. In another embodiment, the method includes administering a composition of the agent under the tongue, to the skin, or to the conjunctiva of the subject. The agent can then be absorbed through a mucosa or epithelium and transported to the central nervous system of the mammal. In one embodiment, the method includes administering the agent in a manner such that the agent is absorbed through the tissue and transported into the central nervous system of the mammal by a neural pathway and in an amount effective to provide a protective or therapeutic effect on a cell of the central nervous system.

The composition can be of any form suitable for administration by these routes and can include a carrier that facilitates absorption of the agent, transport of the agent by a neural pathway, and/or transport of the agent to the CNS, brain, and/or spinal cord. Preferred compositions include one or more of a solubility enhancing additive, a hydrophilic additive, an absorption promoting additive, a cationic surfactant, a viscosity enhancing additive, or a sustained release matrix or composition, a lipid based carrier, preferably a micellar or liposomal composition, a bilayer destabilizing additive, or a fusogenic additive. The composition can be formulated as a cosmetic for dermal delivery.

Agents that can be administered according to the invention include an organic pharmaceutical, an inorganic molecule, a peptide, a peptoid, a protein, a lipid, or a carbohydrate, or a nucleic acid. Preferred agents include GM-1 ganglioside, fibroblast growth factor, particularly basic fibroblast growth factor (bFGF), insulin-like growth factor, particularly insulin-like growth factor-I (IGF-I), nerve growth factor (NGF), phosphatidylserine, a plasmid or vector, and an antisense oligonucleotide.

DETAILED DESCRIPTION OF THE INVENTION

Routes of Administration

Structure and Location of the Trigeminal Nerve

The method of the invention administers the agent to tissue innervated by the trigeminal nerve and outside the nasal cavity. The trigeminal nerve innervates tissues of a mammal's (e.g. human) head including skin of the face and scalp, oral tissues, and tissues of and surrounding the eye. The trigeminal nerve has three major branches, the ophthalmic nerve, the maxillary nerve, and the mandibular nerve. The method of the invention can administer the agent to tissue innervated by one or more of these branches. From there, the agent reaches the CNS.

The Ophthalmic Nerve and Its Branches

The method of the invention can administer the agent to tissue innervated by the ophthalmic nerve branch of the trigeminal nerve. The ophthalmic nerve innervates tissues including superficial and deep parts of the superior region of the face, such as the eye, the lacrimal gland, the conjunctiva, and skin of the scalp, forehead, upper eyelid, and nose. From there, the agent reaches the CNS.

The ophthalmic nerve has three branches known as the nasociliary nerve, the frontal nerve, and the lacrimal nerve. The method of the invention can administer the agent to tissue innervated by one or more branches of the ophthalmic nerve. The frontal nerve and its branches innervate tissues including the upper eyelid, the scalp, particularly the front of the scalp, and the forehead, particularly the middle part of the forehead. Preferably, the method of the invention administers the agent to the frontal nerve. The nasociliary nerve forms several branches including the long ciliary nerves, the ganglionic branches, the ethmoidal nerves, and the infratrochlear nerve. The long ciliary nerves innervate tissues including the eyeball. Preferably the method of the invention administers agent to the long ciliary nerves. The posterior and anterior ethmoidal nerves innervate tissues including the ethmoidal sinus and the nasal cavity. The external nasal branch of the anterior ethmoidal nerve innervates the tip of the nose. The infratrochlear nerve innervates tissues including the upper eyelid and the lacrimal sack. Preferably, the present method administers the agent to the long ciliary nerve, the external nasal branch of the anterior ethmoidal nerve, and/or to the infratrochlear nerve. More preferably, the method of the invention administers the agent to the external nasal branch of the anterior ethmoidal nerve or the infratrochlear nerve. More preferably, this method administers the agent to the infratrochlear nerve. The lacrimal nerve innervates tissues including the lacrimal gland, the conjunctiva, and the upper eyelid. Preferably, the method of the invention administers the agent to the lacrimal nerve.

The Maxillary Nerve and Its Branches

The method of the invention can administer the agent to tissue innervated by the maxillary nerve branch of the trigeminal nerve. The maxillary nerve innervates tissues including the roots of several teeth and facial skin, such as skin on the nose, the upper lip, the lower eyelid, over the cheek bone, over the temporal region. The maxillary nerve has branches including the infraorbital nerve, the zygomaticofacial nerve, the zygomaticotemporal nerve, the nasopalatine nerve, the greater palatine nerve, the posterior superior alveolar nerves, the middle superior alveolar nerve, and the interior superior alveolar nerve. The method of the invention can administer the agent to tissue innervated by one or more branches of the maxillary nerve. From there, the agent reaches the CNS.

The infraorbital nerve innervates tissue including skin on the lateral aspect of the nose, upper lip, and lower eyelid. Preferably, the method of the invention administers the agent to the infraorbital nerve. The zygomaticofacial nerve innervates tissues including skin of the face over the zygomatic bone (cheek bone). Preferably, the method of the invention administers the agent to the zygomaticofacial nerve. The zygomaticotemporal nerve innervates tissue including the skin over the temporal region. The method of the invention can administer the agent to the zygomaticotemporal nerve. The posterior superior alveolar nerves innervate tissues including the maxillary sinus and the roots of the maxillary molar teeth. The method of the invention can administer the agent to the posterior superior alveolar nerves, preferably to portions innervating the roots of the maxillary molar teeth. The middle superior alveolar nerve innervates tissues including the mucosa of the maxillary sinus, the roots of the maxillary premolar teeth, and the mesiobuccal root of the first molar tooth. The method of the invention can administer the agent to the middle superior alveolar nerves, preferably to portions innervating the roots of the maxillary premolar teeth, and the mesiobuccal root of the first molar tooth. The anterior superior alveolar nerve innervates tissues including the maxillary sinus, the nasal septum, and the roots of the maxillary central and lateral incisors and canine teeth. The method of the invention can administer the agent to the anterior superior alveolar nerve, preferably to portions innervating the roots of the maxillary central and lateral incisors and canine teeth.

The Mandibular Nerve and Its Branches

The method of the invention can administer the agent to tissue innervated by the mandibular nerve branch of the trigeminal nerve. The mandibular nerve innervates tissues including the teeth, the gums, the floor of the oral cavity, the tongue, the cheek, the chin, the lower lip, tissues in and around the ear, the muscles of mastication, and skin including the temporal region, the lateral part of the scalp, and most of the lower part of the face. Preferably, the present method administers the agent to the mandibular nerve. From there, the agent reaches the CNS.

The mandibular nerve has branches including the buccal nerve, the auriculotemporal nerve, the inferior alveolar nerve, and the lingual nerve. The method of the invention can administer the agent to one or more of the branches of the mandibular nerve. The buccal nerve innervates tissues including the cheek, particularly the skin of the cheek over the buccinator muscle and the mucous membrane lining the cheek, and the mandibular buccal gingiva (gum), in particular the posterior part of the buccal surface of the gingiva. Preferably, the method of the invention administers the agent to the buccal nerve. The auriculotemporal nerve innervates tissues including the auricle, the external acoustic meatus, the tympanic membrane (eardrum), and skin in the temporal region, particularly the skin of the temple and the lateral part of the scalp. The present method can administer the agent to the auriculotemporal nerve. The inferior alveolar nerve innervates tissues including the mandibular teeth, in particular the incisor teeth, the gingiva adjacent the incisor teeth, the mucosa of the lower lip, the skin of the chin, the skin of the lower lip, and the labial mandibular gingivae. Preferably, the method of the invention administers the agent to the inferior alveolar nerve. The lingual nerve innervates tissues including the tongue, particularly the anterior two-thirds of the tongue, the floor of the mouth, and the gingivae of the mandibular teeth. Preferably, the method of the invention administers the agent to the lingual nerve.

Tissues Innervated by the Trigeminal Nerve

The method of the invention can administer the agent to any of a variety of tissues innervated by the trigeminal nerve. For example, the method can administer the agent to skin, epithelium, or mucosa of or around the face, the eye, the oral cavity, or the ear.

Preferably, the method of the invention administers the agent to skin innervated by the trigeminal nerve. For example, the present method can administer the agent to skin of the face, scalp, or temporal region. Suitable skin of the face includes skin of the chin; the upper lip, the lower lip; the forehead, particularly the middle part of the forehead; the nose, including the tip of the nose, the dorsum of the nose, and the lateral aspect of the nose; the cheek, particularly the skin of the cheek over the buccinator muscle or skin over the cheek bone; skin around the eye, particularly the upper eyelid and the lower eyelid; or a combination thereof. Suitable skin of the scalp includes the front of the scalp, scalp over the temporal region, the lateral part of the scalp, or a combination thereof. Suitable skin of the temporal region includes the temple and scalp over the temporal region. Preferred regions of skin for administering the agent include those portions nearest the trigeminal nerve and its nerve endings.

Preferably, the method of the invention administers the agent to mucosa or epithelium innervated by the trigeminal nerve. For example, the present method can administer the agent to mucosa or epithelium of or surrounding the eye, such as mucosa or epithelium of the upper eyelid, the lower eyelid, the eyeballs, the conjunctiva, the lacrimal system, or a combination thereof. The method of the invention can also administer the agent to mucosa or epithelium of the oral cavity, such as mucosa or epithelium of the tongue; particularly the anterior two-thirds of the tongue and under the tongue; the cheek; the lower lip; the upper lip; the floor of the oral cavity; the gingivae (gums), in particular the gingiva adjacent the incisor teeth, the labial mandibular gingivae, and the gingivae of the mandibular teeth; or a combination thereof. Preferred regions of mucosa or epithelium for administering the agent include the tongue, particularly sublingual mucosa or epithelium, the conjunctiva, the lacrimal system, particularly the palpebral portion of the lacrimal gland and the nasolacrimal ducts, the mucosa of the lower eyelid, the mucosa of the cheek, or a combination thereof.

Preferably, the method of the invention administers the agent to oral tissues innervated by the trigeminal nerve. For example, the present method can administer the agent to oral tissues such as the teeth, the gums, the floor of the oral cavity, the cheeks, the lips, the tongue, particularly the anterior two-thirds of the tongue, or a combination thereof. Suitable teeth include mandibular teeth, such as the incisor teeth. Suitable portions of the teeth include the roots of several teeth, such as the roots of the maxillary molar teeth, the maxillary premolar teeth, the maxillary central and lateral incisors, the canine teeth, and the mesiobuccal root of the first molar tooth, or a combination thereof. Suitable portions of the lips include the skin and mucosa of the upper and lower lips. Suitable gums include the gingiva adjacent the incisor teeth, and the gingivae of the mandibular teeth, such as the labial mandibular gingivae, or a combination thereof. Suitable portions of the cheek include the skin of the cheek over the buccinator muscle, the mucous membrane lining the cheek, and the mandibular buccal gingiva (gum), in particular the posterior part of the buccal surface of the gingiva, or a combination thereof. Preferred oral tissue for administering the agent includes the tongue, particularly sublingual mucosa or epithelium, the mucosa inside the lower lip, the mucosa of the cheek, or a combination thereof.

Preferably, the method of the invention administers the agent to a tissue of or around the eye that is innervated by the trigeminal nerve. For example, the present method can administer the agent to tissue including the eye, the conjunctiva, the lacrimal gland including the lacrimal sack, the nasolacrimal ducts, the skin or mucosa of the upper or lower eyelid, or a combination thereof. Preferred tissue of or around the eye for administering the agent includes the conjunctiva, the lachrimal system, the skin or mucosa of the eyelid, or a combination thereof. Agent that is administered conjunctivally but not absorbed through the conjunctival mucosa can drain through nasolacrimal ducts into the nose, where it can be transported to the CNS, brain, and/or spinal cord as though it had been intranasally administered.

Preferably, the method of the invention administers the agent to a tissue of or around the ear that is innervated by the trigeminal nerve. For example, the present method can administer the agent to tissue including the auricle, the external acoustic meatus, the tympanic membrane (eardrum), and the skin in the temporal region, particularly the skin of the temple and the lateral part of the scalp, or a combination thereof. Preferred tissue of or around the ear for administering the agent includes the skin of the temple.

The method of the invention can administer the agent to any of a variety of branches of the trigeminal nerve, and branches of these branches, that innervate tissues outside the nasal cavity. Branches of the trigeminal nerve that innervate tissues outside the nasal cavity include the ophthalmic nerve, the maxillary nerve, and the mandibular nerve.

Branches of the ophthalmic nerve branch of the trigeminal nerve that innervate tissues outside the nasal cavity include the nasociliary nerve, the frontal nerve, and the lacrimal nerve. Preferably, the method of the invention administers the agent to the frontal nerve and/or the lacrimal nerve. Preferably, the method of the invention administers the agent to a branch of the nasociliary nerve such as the long ciliary nerve, the external nasal branch of the anterior ethmoidal nerve, and/or to the infratrochlear nerve, more preferably to the external nasal branch of the anterior ethmoidal nerve and/or the infratrochlear nerve, more preferably to the infratrochlear nerve.

Branches of the maxillary nerve branch of the trigeminal nerve that innervate tissues outside the nasal cavity include the infraorbital nerve, the zygomaticofacial nerve, the zygomaticotemporal nerve, the posterior superior alveolar nerves, the middle superior alveolar nerve, and the interior superior alveolar nerve. Preferably, the method of the invention administers the agent to the infraorbital nerve, the zygomaticofacial nerve, portions of the posterior superior alveolar nerves innervating the roots of the maxillary molar teeth, portions of the middle superior alveolar nerves innervating the roots of the maxillary premolar teeth, and the mesiobuccal root of the first molar tooth, portions of the anterior superior alveolar nerve innervating the roots of the maxillary central and lateral incisors and canine teeth, or a combination thereof.

Branches of the mandibular nerve branch of the trigeminal nerve that innervate tissues outside the nasal cavity include the buccal nerve, the auriculotemporal nerve, the inferior alveolar nerve, and the lingual nerve. Preferably, the present method administers the agent to the buccal nerve, the inferior alveolar nerve, and/or the lingual nerve.

Preferably, the method of the present invention administers the agent through the skin or the mucosa or epithelium of the tongue, mouth, or conjunctiva. Preferably, the method of the present invention administers the agent under the tongue of, onto the skin of, or onto the conjunctiva of a subject for the delivery of the agent to the subject's central nervous system (CNS) or brain. According to the invention, an agent can be administered, for example, through the oral, lingual, and/or conjunctival mucosa and/or epithelium; or through the skin of the face, forehead, upper eyelid, lower eyelid, side of the nose, upper lip, cheek, chin, scalp and teeth.

The method can involve movement of an agent into or through a tissue and, for example, along a neural pathway to the CNS, into perivascular channels, and into prelymphatic channels or lymphatics, which are associated with the brain and spinal cord. Certain agents can enter the cerebrospinal fluid and then or also enter the CNS, brain, and/or spinal cord. The method can deliver the agent to one or more portions of the CNS or brain including: a cerebellum, a brain stem, a spinal cord, an hippocampal formation, an amygdaloid nuclei, a nucleus basalis of Meynert, a locus ceruleus, a meninges, a cortical or subcortical structure, an olfactory bulb, a parenchymal tissue of an olfactory bulb, a midbrain, a diencephalon, a medulla a ventral dura, and the like. Typically, the agent is administered for the diagnosis, prevention, or treatment of CNS, brain, and/or spinal cord disorders.

In one embodiment, the method of the invention includes administering the agent alone to a tissue innervated by the trigeminal nerve. In this instance, the chemical characteristics of the agent itself can facilitate its transport to diseased or damaged neurons or cells in the CNS, brain, and/or spinal cord. Alternatively, the agent may be combined with other substances that assist in transporting the agent to sites of damaged neurons. It is preferred that auxiliary substances are capable of delivering the agent to peripheral sensory neurons or along neural pathways to dysfunctioning areas of the central nervous system.

The present invention relates to administering the agent to tissues that are innervated by the trigeminal nerve and outside the nasal cavity. Tissues that are innervated by the trigeminal nerve and are outside the nasal cavity can be referred to as extra-nasal tissues innervated by the trigeminal nerve, or as extranasal tissues surrounding the trigeminal nerve. Similarly, epithelium outside the nasal cavity can be referred to herein as extra-nasal epithelium, mucosa outside the nasal cavity can be referred to herein as extra-nasal mucosa, and skin or dermal tissue outside the nasal cavity can be referred to herein as extra-nasal skin or dermal tissue.

Agents for Delivery to the Central Nervous System

The present method can administer a variety of different agents to the central nervous system. In general, the method of the invention can administer an agent that can be employed for diagnosis, prevention, or treatment of a disease or disorder affecting the CNS, brain, and/or spinal cord; that can nourish or maintain a cell or tissue in the CNS, brain, and/or spinal cord; that can prevent or inhibit degradation of a cell or tissue in the CNS, brain, and/or spinal cord; that can alter gene expression in a cell or tissue in the CNS, brain, and/or spinal cord; that can regulate a functional activity of a cell or tissue in the CNS, brain, and/or spinal cord; that can regulate growth of a cell or tissue in the CNS, brain, and/or spinal cord; or the like.

Certain agents are not or are only poorly transported across the blood-brain barrier. For such agents, an effective amount of the agent does not readily, and may not ever, cross the blood-brain barrier. The present method can effectively deliver such agents to the CNS, brain, and/or spinal cord.

Administration of agents by the method of the invention can more effectively deliver the agent to the CNS, brain and/or spinal cord, can decrease the amount of agent administered outside the CNS, brain and/or spinal cord, and, preferably, can decrease the undesirable systemic effects of the agent. More effective or efficient delivery of the agent to the CNS, brain and/or spinal cord can decrease the total dose of agent administered. Alternatively, such effective delivery of agent can decrease the amount of agent that reaches undesired destinations within the subject but outside the CNS, brain and/or spinal cord. This more effective delivery results in less of such an agent in locations within the subject where it can have undesirable effects.

Lipophilicity is yet another preferred property of an agent. It is preferred that the agent is lipophilic to promote absorption into surface tissue, such as oral, or conjunctival epithelium or skin; and along a neuron, such as a trigeminal neuron. A preferred agent is at least partially soluble in fluids that surround termini of the trigeminal nerve to be absorbed into the trigeminal neuron and its associated lymphatic and/or perivascular channels, fluids that are secreted by the mucous membranes that surround the neurons contained within the oral or conjunctival mucosa, or the like.

The agent can be an organic pharmaceutical, an inorganic molecule, a peptide, a peptoid, a protein, a lipid, or carbohydrate, a nucleic acid, or the like.

An organic pharmaceutical can be a stimulant, a sedative, an hypnotic, an analgesic, an anticonvulsant, an antihypertensive, an antiemetic, an anxiolytic, an antidepressant, a tranquilizer, a cognition enhancer, a narcotic antagonist or agonist, a vitamin or nutrient, an enzyme inhibitor, an antioxidant, a free radical scavenger, a metal chelating agent, an agent which can alter the activity of an ion channel, an antineoplastic, an anti-inflammatory, or a combination thereof. Advantageously, an organic pharmaceutical modulates a functional activity of an enzyme, receptor, cell, or tissue in the CNS, brain, and/or spinal cord. A preferred agent that can regulate a functional activity includes, for example, a neurotransmitter, a neuromodulator, a nootropic, a receptor agonist or antagonist, or a combination thereof.

The organic pharmaceutical can be an antiviral, an antibacterial, an antiparasitic, an antifungal, or a combination thereof. Preferred agents for diagnosis, prevention or treatment of an infection of the CNS, brain, and/or spinal cord include an antibacterial, an antiparasitic, and/or an antifungal agent. Preferred antiviral agents include agents that stop or inhibit the replication or spread of viruses such as adenoviruses, arboviruses, enteroviruses, rabies viruses, and HIV.

A preferred agent can prevent or inhibit degradation of a cell or tissue of the CNS, brain, and/or spinal cord. Such an agent can act by preventing or inhibiting oxidative stress or free radical damage.

An inorganic agent can be an antioxidant or an anti-cancer agent (e.g. cisplatin).

A peptide or protein agent can be a hormone, a hormone releasing factor, a growth factor, an enzyme, an antibody, a catalytic antibody, a receptor, a receptor ligand, a neurotrophin, or the like having an effect on a cell or tissue in the CNS, brain, and/or spinal cord. Suitable hormones include a platelet derived growth factor (PDGF e.g. alpha PDGF), a transforming growth factor (TGF e.g. TGF-β). A peptide or protein agent can regulate growth of a cell or tissue of the CNS, brain, and/or spinal cord.

The method of the invention can deliver a peptoid agent. As used herein peptoid refers to a nonnatural peptide in which conventional amino acid-amino acid peptide bonds are substituted with bonds that provide resistance to proteases. A peptoid can also contain substitutes for conventional amino acids. Peptoids are described in U.S. Pat. No. 5,811,387, which is incorporated herein by reference. Advantageously, a peptoid modulates the activity of an enzyme, receptor, cell, or tissue in the CNS, brain, and/or spinal cord. Nucleic acid agents include DNA or RNA vectors or plasmids that encode one or more protein agents, such as a growth factor, neurotrophin, enzyme (e.g. superoxide dismutase or catalase), receptor, or the like. Plasmids and vectors for delivery of a coding sequence to a mammalian tissue are known to those of skill in the art. A retrovirus is a preferred RNA containing vector. Nucleic acid agents also include ribozymes and antisense molecules. Such ribozymes and antisense constructs include agents that modulate the expression of one or more genes in the CNS, brain, and/or spinal cord. Preferred antisense constructs include those that either cleave or bind the mRNAs coding for the growth factors such as VEGF, FGF, NGF and the like. The ribozymes and antisense molecules may also be targeted against certain proteases such as MMPs (matrix metalloproteinases).

The interest in gene therapy as a means of treating inherited or acquired diseases has led to the development of methods for transferring genetic information, more particularly for delivering nucleotide sequences encoding human genes using viral-mediated gene transfer systems. Such viral-mediated gene transfer systems enable delivery of desired genetic information, in this case a nucleotide sequence encoding an agent, preferably a neurologic agent, to a selected cell or tissue and its subsequent expression there under the direction of the viral promoter. Viral-mediated gene transfer systems are known in the art. See, for example, U.S. Pat. Nos. 5,707,618; 5,714,353; and 5,672,344. In this manner, increases in the amount of agent to a therapeutically effective level can be achieved in vivo by increasing production of the agent.

Neurologic Agents

Neurologic agents are one preferred category of agents that can be administered according the present invention. A neurologic agent employed in the method of the present invention can be any substance that promotes the function or survival of neurons and prevents the loss or further loss of nerve cells. For example, a preferred neurologic agent can promote nerve or glial cell growth, promote survival of functioning cells, augment the activity of functioning cells, enhance the synthesis of neurotransmitter substances, augment the activity of naturally occurring nerve growth promoting factors, act as a nerve growth promoting factor, prevent degeneration of neurons, induce regrowth of dendrite and axon, have more than one of these properties, or the like. A preferred neurologic agent is a neurotrophic and/or neuritogenic factor that is similar to a naturally occurring nerve growth promoting substance. Numerous of such neurologic agents are known to those of skill in the art.

Among the preferred neurologic agents are proteins, growth factors, and neurotrophins such as nerve growth factor (NGF), neurotrophins 3, 4, and/or 5 (NT-3, NT-4 and/or NT-5), brain-derived neurotrophic factor (BDNF), fibroblast growth factors (FGFs, e.g., basic fibroblast growth factor), insulin, insulin-like growth factors (IGFs, e.g., IGF-I and/or IGF-II), ciliary neurotrophic factor (CNTF), glia-derived neurotrophic factor (GDNF), glia-derived nexin, combinations thereof, and the like. Additional preferred neurologic agents include lipophilic compounds such as a ganglioside (e.g. GM-1 ganglioside), a phosphatidylserine (PS), combinations thereof, and the like. Other preferred neurologic agents include a cholinergic enhancing factor, such as phosphoethanolamine and thyroid hormone T.3, agonists of an acetylcholine receptor, such as of a muscarinic or a nicotinic acetylcholine receptor (e.g. Xomaline), anticholinesterase agents (e.g. Aricept (donepezil hydrochloride), Exelon, Cognex (Tacrine), tetrahydroaminoacridine, or heptylphyostigmine), combinations thereof, and the like. Additional preferred agents include estrogen, Vitamin E, and other antioxidants. GM-1 ganglioside, fibroblast growth factor, particularly basic fibroblast growth factor (bFGF), insulin-like growth factor, particularly insulin-like growth factor-I (IGF-I), nerve growth factor (NGF), are more preferred.

Preferred neurologic agents also include DNA or RNA vectors or plasmids that encode one or more protein neurologic agents or nerve growth promoting factors, such as fibroblast growth factor, particularly basic fibroblast growth factor (bFGF), insulin-like growth factor, particularly insulin-like growth factor-I (IGF-I), nerve growth factor (NGF), or the like. Plasmids and vectors for delivery of a coding sequence to a mammalian tissue are known to those of skill in the art. A retrovirus is a preferred RNA containing vector.

Further, certain ribozymes and antisense molecules are neurologic agents. Such ribozymes and antisense constructs include agents that modulate the expression of an endogenous neurologic agent, such as fibroblast growth factor, particularly basic fibroblast growth factor (bFGF), insulin-like growth factor, particularly insulin-like growth factor-I (IGF-I), nerve growth factor (NGF), or the like.

Certain neurologic agents are not or are only poorly transported across the blood-brain barrier. For such agents, an effective amount of the neurologic agent does not readily, and may not ever, cross the blood-brain barrier. The present method can effectively deliver such neurologic agents to the CNS, brain, and/or spinal cord.

Administration of neurologic agents by the method of the invention can more effectively deliver the agent to the CNS, brain and/or spinal cord, can decrease the amount of agent administered outside the CNS, brain and/or spinal cord, and, can preferably, decrease the undesirable systemic effects of the agent. More effective or efficient delivery of the neurologic agent to the CNS, brain and/or spinal cord can decrease the total dose of agent administered. Alternatively such effective delivery of agent can decrease the amount of agent that reaches undesired destinations within the subject but outside the CNS, brain and/or spinal cord. This more effective delivery results in less of such an agent in locations within the subject where it can have undesirable effects.

Another preferred property for a neurologic agent is that it can facilitate its movement into the CNS. Such neurologic agents typically are readily incorporated into nerve cell membranes or have an affinity for nerve cell receptor sites. Such an agent is typically naturally synthesized in tissues in response to neural stimulation and subsequently binds to receptors on neurons where they act as a nerve growth promoting factors.

Lipophilicity is yet another preferred property of a neurologic agent. It is preferred that the neurologic agent is lipophilic to promote absorption into surface tissue, such as oral, or conjunctival epithelium or skin; and along a neuron, such as a trigeminal neuron. A preferred neurologic agent is at least partially soluble in fluids that surround termini of the trigeminal nerve to be absorbed into the trigeminal neuron and its associated lymphatic channels, fluids that are secreted by the mucous membranes that surround the neurons contained within the oral or conjunctival mucosa, or the like. Among those neurologic agents that are lipophilic are gangliosides (such as GM-1 ganglioside) and phosphatidylserine (PS).

IGF-I

The term "IGF-I" as used herein refers to insulin-like growth factor I (IGF-I), a single chain peptide having 70 amino acids and a molecular weight of about 7,600 daltons. Insulin-like growth factor I stimulates mitosis and growth processes associated with cell development.

In one embodiment of the invention, increasing in the amount of IGF-I to a therapeutically effective level is achieved via administration of a pharmaceutical composition including a therapeutically effective dose. The IGF-I to be administered can be from any animal species including, but not limited to, rodent, avian, canine, bovine, porcine, equine, and, preferably, human. Preferably the IGF-I is from a mammalian species, and more preferably is from a mammal of the same species as the mammal undergoing treatment.

Biologically active variants of IGF-I are also encompassed by the method of the present invention. Such variants should retain IGF-I activities, particularly the ability to bind to IGF-I receptor sites. IGF-I activity may be measured using standard IGF-I bioassays. Representative assays include known radioreceptor assays using placental membranes (see, e.g., U.S. Pat. No. 5,324,639; Hall et al. (1974) *J. Clin. Endocrinol. and Metab.* 39:973-976; and Marshall et al. (1974) *J. Clin. Endocrinol. and Metab.* 39:283-292), a bioassay that measures the ability of the molecule to enhance incorporation of tritiated thymidine, in a dose-dependent manner, into the DNA of BALB/c 3T3 fibroblasts (see, e.g., Tamura et al. (1989) *J. Biol. Chem.* 262:5616-5621), and the like; herein incorporated by reference. Preferably, the variant has at least the same activity as the native molecule.

Suitable biologically active variants can be IGF-I fragments, analogues, and derivatives. By "IGF-I fragment" is intended a protein consisting of only a part of the intact IGF-I sequence and structure, and can be a C-terminal deletion or N-terminal deletion of IGF-I. By "analogue" is intended an analogue of either IGF-I or an IGF-I fragment that include a native IGF-I sequence and structure having one or more amino acid substitutions, insertions, or deletions. Peptides having one or more peptoids (peptide mimics) are also encompassed by the term analogue (see e.g. International Publication No. WO 91/04282). By "derivative" is intended any suitable modification of IGF-I, IGF-I fragments, or their respective analogues, such as glycosylation, phosphorylation, or other addition of foreign moieties, so long as the IGF-I activity is retained. Methods for making IGF-I fragments, analogues, and derivatives are available in the art. See generally U.S. Pat. Nos. 4,738,921, 5,158,875, and 5,077,276; International Publication Nos. WO 85/00831, WO 92/04363, WO 87/01038, and WO 89/05822; and European Patent Nos. EP 135094, EP 123228, and EP 128733; herein incorporated by reference.

IGF-I variants will generally have at least 70%, preferably 80%, more preferably 85%, even more preferably 90% to 95% or more, and most preferably 98% or more amino acid sequence identity to the amino acid sequence of the reference IGF-I molecule. A variant may, for example, differ by as few as 1 to 10 amino acid residues, such as 6-10, as few as 5, as few as 4, 3, 2, or even 1 amino acid residue.

By "sequence identity" is intended the same amino acid residues are found within the variant sequence and a reference sequence when a specified, contiguous segment of the amino acid sequence of the variant is aligned and compared to the amino acid sequence of the reference sequence. Methods for sequence alignment and for determining identity between sequences are well known in the art. See, for example, Ausubel et al., eds. (1995) *Current Protocols in Molecular Biology*, Chapter 19 (Greene Publishing and Wiley-Interscience, New York); and the ALIGN program (Dayhoff (1978) in *Atlas of Protein Sequence and Structure* 5:Suppl. 3 (National Biomedical Research Foundation, Washington, D.C.). A number of algorithms are available for aligning sequences and determining sequence identity and include, for example, the homology alignment algorithm of Needleman et al. (1970) *J. Mol. Biol.* 48:443; the local homology algorithm of Smith et al. (1981) *Adv. Appl. Math.* 2:482; the search for similarity method of Pearson et al. (1988) *Proc. Natl. Acad. Sci.* 85:2444; the Smith-Waterman algorithm (*Meth. Mol. Biol.* 70:173-187 (1997); and BLASTP, BLASTN, and BLASTX algorithms (see Altschul et al. (1990) *J. Mol. Biol.* 215:403-410). Computerized programs using these algorithms are also available, and include, but are not limited to: GAP, BESTFIT, BLAST, FASTA, and TFASTA, available in the Genetics Computing Group (GCG) package, Version 8, Madison, Wis., USA; and CLUSTAL in the PC/Gene program by Intelligenetics, Mountain View, Calif. Preferably, the sequence identity is determined using the default parameters determined by the program.

With respect to optimal alignment of two amino acid sequences, the contiguous segment of the variant amino acid sequence may have additional amino acid residues or deleted amino acid residues with respect to the reference amino acid sequence. The contiguous segment used for comparison to the reference amino acid sequence will include at least 20 contiguous amino acid residues, and may be 30, 40, 50, or more amino acid residues. Corrections for increased sequence identity associated with inclusion of gaps in the variant's amino acid sequence can be made by assigning gap penalties.

When considering percentage of amino acid sequence identity, some amino acid residue positions may differ as a result of conservative amino acid substitutions, which do not affect properties of protein function. In these instances, percent sequence identity may be adjusted upwards to account for the similarity in conservatively substituted amino acids. Such adjustments are well known in the art. See, for example, Meyers & Miller (1988) *Computer Applic. Biol. Sci.* 4:11-17.

The art provides substantial guidance regarding the preparation and use of such IGF-I variants, as discussed further below. A fragment of IGF-I will generally include at least about 10 contiguous amino acid residues of the full-length molecule, preferably about 15-25 contiguous amino acid residues of the full-length molecule, and most preferably about 20-50 or more contiguous amino acid residues of full-length IGF-I.

Several IGF-I analogues and fragments are known in the art and include those described in, for example, *Proc. Natl. Acad. Sci. USA* 83 (1986) 4904-4907; *Biochem. Biophys. Res. Commun.* 149 (1987) 398-404; *J. Biol. Chem.* 263 (1988) 6233-6239; *Biochem. Biophys. Res. Commun.* 165 (1989) 766-771; Forsbert et al. (1990) *Biochem. J.* 271:357-363; U.S. Pat. Nos. 4,876,242 and 5,077,276; and International Publication Nos. WO 87/01038 and WO 89/05822. Representative analogues include one with a deletion of Glu-3 of the mature molecule, analogues with up to 5 amino acids truncated from the N-terminus, an analogue with a truncation of the first 3 N-terminal amino acids (referred to as des(1-3)-IGF-I, des-IGF-I, tIGF-I, or brain IGF), and an analogue including the first 17 amino acids of the B chain of human insulin in place of the first 16 amino acids of human IGF-I.

The IGF-I used in the present invention can be in its substantially purified, native, recombinantly produced, or chemically synthesized forms. IGF-I can be isolated and purified from serum or plasma (see Phillips (1980) *New Eng. J Med.* 302: 371-380, and European Patent No. EP 123,228). IGF-I can also be chemically synthesized by the solid phase method (see Li et al. (1983) *Proc. Natl. Acad. Sci. USA* 80: 2216-2220). These references are herein incorporated by reference.

Genetic engineering by recombinant DNA techniques can be the most efficient way of producing IGF-I. The human DNA sequence encoding IGF-I is known and can be introduced into host cells for expression. IGF-I can be produced by recombinant DNA techniques in *E. coli*, yeast, insect, and mammalian cells. Secreted IGF-I can be made by adding a signal sequence to the DNA sequence encoding IGF-I. In addition, the DNA sequence encoding IGF-I can be manipulated to make IGF-I fragments, analogues, or derivatives. Such recombinant DNA techniques are generally available in the art. See, for example, International Publication No. WO 96/07424, where recombinant human IGF-I protein is produced in yeast. IGF-I can also be recombinantly produced in the yeast strain *Pichia pastoris* and purified essentially as described in U.S. Pat. Nos. 5,324,639, 5,324,660, and 5,650,496 and International Publication No. WO 96/40776.

FGF

By the term "FGF," as used herein, is meant a fibroblast growth factor protein such as FGF-1, FGF-2, FGF-4, FGF-6, FGF-8, FGF-9 or FGF-98, or a biologically active fragment or mutein thereof. Typically, the FGF is human (h) FGF-1, bovine (b) FGF-1, hFGF-2, bFGF-2, hFGF-4 or hFGF-5. In an alternative embodiment, the active agent in the unit does is hFGF-6, hFGF-8, hFGF-9 or hFGF-98. In one embodiment of the invention, increasing in the amount of FGF to a therapeutically effective level is achieved via administration of a pharmaceutical composition including a therapeutically effective dose. The FGF to be administered can be from any animal species including, but not limited to, rodent, avian, canine, bovine, porcine, equine, and, preferably, human. Preferably the FGF is from a mammalian species, and more preferably is from a mammal of the same species as the mammal undergoing treatment.

The amino acid sequences and method for making many of the FGFs that are employed in the unit dose pharmaceutical composition and method of the present invention are well known in the art. In particular, references disclosing the amino acid sequence and recombinant expression of FGF 1-9 and FGF-98 are discussed sequentially below.

FGF-1:The amino acid sequence of HFGF-1 and a method for its recombinant expression are disclosed in U.S. Pat. No. 5,604,293 (Fiddes), entitled "Recombinant Human Basic Fibroblast Growth Factor," which issued on Feb. 18, 1997. See FIG. 2d of the '293 patent. This reference and all other references in the section headed FGF whether cited before or after this sentence, are expressly incorporated herein by reference in their entirety. The amino acid sequence of bFGF-1 is disclosed in U.S. Pat. No. 5,604,293 (Fiddes) at FIG. 1b, as is a method for its expression. The mature forms of both HFGF-1 and bFGF-1 have 140 amino acid residues. bFGF-1 differs from HFGF-1 at 19 residue positions: 5 Pro to Leu, 21 His to Tyr, 31 Tyr to Val, 35 Arg to Lys, 40 Gin to Gly, 45 Gin to Phe, 47 Ser to Cys, 51 Tyr to Ile, 54 Tyr to Val, 64 Tyr to Phe, 80 Asn to Asp, 106 Asn to His, 109 Tyr to Val, 116 Ser to Arg, 117 Cys to Ser, 119 Arg to Leu, 120 Gly to Glu, 125 Tyrto Phe and 137 Tyr to Val. In most instances, the differences are conserved. Further, the differences at residue positions 116 and 119 merely interchange the position of the Arg.

FGF-2:The amino acid sequence of human FGF-2 (hFGF-2) and methods for its recombinant expression are disclosed in U.S. Pat. No. 5,439,818 (Fiddes) entitled "DNA Encoding Human Recombinant Basic Fibroblast Growth Factor," which issued on Aug. 8, 1995 (see FIG. 4 therein). The amino acid sequence of bovine FGF-2 (bFGF-2) and various methods for its recombinant expression are disclosed in U.S. Pat. No. 5,155,214, entitled "Basic Fibroblast Growth Factor," which issued on Oct. 13, 1992. When the 146 residue forms of hFGF-2 and bFGF-2 are compared, their amino acid sequences are nearly identical with only two residues that differ. In particular, in going from hFGF-2 to bFGF-2, the sole differences occur at residue positions 112(Thr to Ser) and 128(Ser to Pro).

FGF-3:FGF-3 was first identified as an expression product of a mouse int-2 mammary tumor and its amino acid sequence is disclosed in Dickson et al., "Potential Oncogene Product Related to Growth Factors," Nature 326:833 (Apr. 30, 1987). FGF-3 which has 243 residues when the N-terminal Met is excluded, is substantially longer than both FGF-2 (human and bovine) and FGF-2 (human and bovine). A comparison of amino acid residues for mFGF-3 relative to bFGF-1 and bFGF-2 is presented in overlap fashion in Dickson, et al. (1987). When the amino acid sequence of mFGF-3 is compared to bFGF-1 and bFGF-2, FGF-3 has 5 locations containing residue inserts relative to both FGF-1 and FGF-2. The most significant of these inserts is a 12 and a 14 residue insert relative to FGF-2 and FGF-1, respectively, beginning at residue position 135 of FGF-3. Allowing for the inserts, Dickson discloses the mFGF-3 has 53 residue identities relative to FGF-1 and 69 residue identifies relative to FGF-2. In addition, FGF-3 contains a hydrophobic N-terminal extension of 10 residues relative to the N-terminus of the signal sequence in both FGF-1 and FGF-2. Relative to the C-terminus of bFGF-1 and bFGF-2, mFGF-3 contains an approximately 60 residue extension. It is unlikely that the C-terninal extension of mFGF-3 is necessary for activity. More likely, it is a moderator of activity by conferring receptor specificity on the FGF.

FGF-4:The amino acid sequence for the hst protein, now known as hFGF-4, was first disclosed by Yoshida, et al., "Genomic Sequence of hst, a Transforming Gene Enclosing a Protein Homologous to Fibroblast Growth Factors and the int-2 Enclosed Protein," PHAS USA, 84:7305-7309 (October 1987) at FIG. 3. Including its leader sequence, hFGF-4 has 206 amino acid residues. When the amino acid sequences of hFGF-4, hFGF-1, hFGF-2 and mFGF-3 are compared, residues 72-204 of hFGF-4 have 43% homology to hFGF-2; residues 79-204 have 38% homology to hFGF-1; and residues 72-174 have 40% homology to MFGF-3. A comparison of these four sequences in overlap form is shown in Yoshida (1987) at FIG. 3. Further, the Cys at residue positions 88 and 155 of hFGF-4 are highly conserved among hFGF-1, hFGF-2, mFGF-3 and hFGF-4 and are found in a homologous region.

The two putative cell binding sites of hFGF-2 occur at residue positions 36-39 and 77-81 thereof. See Yoshida (1987) at FIG. 3. The two putative heparin binding sites of hFGF-2 occur at residue positions 18-22 and 107-111 thereof. See Yoshida (1987) at FIG. 3. Given the substantial similarity between the amino acid sequences for human and bovine FGF-2, we would expect the cell binding sites for bFGF-2 to also be at residue positions 36-39 and 77-81 thereof, and the heparin binding sites to be at residue positions 18-22 and 107-111 thereof. In relation to hFGF-1, the putative cell binding sites occur at residues 27-30 and 69-72, and the putative heparin binding sites occur at residues 9-13 and 98-102. Insofar as mature bFGF-1 has the identical amino acids at residue positions 9-13, 27-30, 69-72 and 98-102 as does mature hFGF-2, bFGF-1 would be expected to have the same cell and heparin binding sites as does hFGF-1.

FGF-5:The cDNA and deduced amino acid sequences for hFGF-5 are disclosed in Zhan, et al., "The Human FGF-5 Oncogene Encodes a Novel Protein Related to Fibroblast Growth Factors," Molec. And Cell. Biol., 8(8):3487-3495 (August 1988) at FIG. 1. Zhan also discloses a method for cloning hFGF-5. Another hFGF-5 has an amino acid sequence which differs from Zhan's sequence at residue position 236 (having a Lys instead of the Zhan's Asn) and at residue position 243 (having a Pro instead of Zhan's Ser). Both amino acid sequences for hFGF-5 have 266 amino acid residues that include a leader sequence of 67 residues upstream of the first residue of mature FGF-2 and a tail sequence that extends about 47 residues beyond the C-terminus of hFGF-2. A comparison between the amino acid sequences of hFGF-1, hFGF-2, mFGF-3, hFGF-4 and FGF-5 is presented in FIG. 2 of Zhan (1988). In FIG. 2 of Zhan, hFGF-1, hFGF-2, mFGRF-3 and hFGF-4 are identified as aFGF (i.e., acidic FGF), bFGF (i.e., basic FGF), int-2, and hstKS3, respectively, i.e., by their original names. In the above referenced comparison, two blocks of FGF-5 amino acid residues (90 to 180 and 187-207) showed substantial homology to FGF 1-4, i.e., 50.4% with FGF-4, 47.5% with FGF-3, 43.4% with FGF-2 and 40.2% with hFGF-1. See Zhan (1988) at FIG. 2 U.S. Pat. No. 5,155,217 (Goldfarb) and U.S. Pat. No. 5,238,916 (Goldfarb), which correspond to the Zhan publication, refer to the FGF-5 of Zhan as FGF-3. However, the art (as evidenced by Coulier below) has come to recognize that the hFGF of Zhan (and of the Goldfarb patents) as FGF-5 and not as FGF-3. The two Goldfarb patents contain the same amino acid sequence for hFGF-5 as reported above by Zhan.

FGF-6:The cDNA and deduced amino acid sequence for hFGF-6 are disclosed in Coulier et al., "Putative Structure of the FGF-6 Gene Product and Role of the Signal Peptide," Oncogene 6:1437-1444 (1991) at FIG. 2. Coulier also discloses a method for cloning FGF-6. hFGF-6 is one of the largest of the FGFs, having 208 amino acid residues. When the amino acid sequences of human FGF-1, FGF-2, FGF-3, FGF-4, FGF-5, FGF-6 and FGF-7 are compared, there are strong similarities in the C-terminal two-thirds of the molecules (corresponding e.g., to residues 78-208 of hFGF-6. In particular, 23 residues of FGF-6, including the two cysteines at residue positions 90-157 of hFGF-6 were identical between the seven members of the family. This number increases to 33 residues when conserved amino acid residues are considered. The overall similarities between these seven human FGFs ranged from 32% to 70% identical residues and 48% to 79% conserved residues for the C-terminal two-thirds of the molecules. The sequence comparisons of hFGF-1 to hFGF-5 and hFGF-7, relative to hfGF-6, are shown in the FGF Table herein.

FGF TABLE

Amino Acid Sequence Comparison of hFGF-6 With Other hFGFs

|  | Identical Residues* | Conserved Residues** | Identical Residues* (%) | Conserved Residues** (%) |
|---|---|---|---|---|
| hFGF-4 | 91 | 103 | 70 | 79 |
| hFGF-5 | 64 | 82 | 49 | 63 |
| hFGF-3 | 55 | 78 | 42 | 60 |
| hFGF-2 | 54 | 69 | 42 | 53 |
| hFGF-7 | 47 | 68 | 36 | 52 |
| hFGF-1 | 42 | 62 | 32 | 48 |

*Number and percentages of identical or conserved residues were calculated for the C-terminal two-thirds of the hFGF6 molecule (residues 78-208).
**Conserved residues are defined according to the structure-genetic matrix of Feng et al., J. Mol. Evol., 21: 112-125 (1985).

Referring to the FGF Table, FGF-6 has the highest correspondence (91 identical residues/10o3 conserved residues) with FGF-4. This amounts to 70% identical and 79% conserved residues. HFGF-6 differed most from hFGF-3, hFGF-2, hFGF-7 and hFGF-1, with 42, 42, 36 and 32; identical residues, respectively.

An overlaid comparison of the amino acid sequences of FGFs 1-7 is shown in FIG. 3 of incorporated Coulier (1991). FIG. 3 of Coulier shows that when in the C-terminal two-thirds of the FGF molecules are aligned, there are 23 residue positions wherein the residues from all seven FGF members are identical. There are also ten residue positions wherein residues from all seven FGF members are conserved. Coulier (1991) at FIG. 3. In combination, these identical and conserved residues form about 6 locations of three to five residues on the terminal two-thirds of each of the FGFs 1-7, wherein three to five residues are grouped together in all seven species of human FGF (i.e, hFGF 1-7).

FGF-7:The amino acid sequence of hFGF-7 is well-known in the art and disclosed in Miyamoto, et.al., "Molecular Cloning of a Novel Cytokine cDNA Encoding the Ninth Member of the Fibroblast Growth Factor Family, Which has a Unique Secretion Property," Mol. And Cell. Biol. 13(7): 4251-4259 (1993) at FIG. 2. In Miyamoto, the hFGF-7 was referred to by its older name "KGF". FGF-7 has 191 amino acid sequences of hFGF-106 and hFGF-9 shows that the carboxy terminal two thirds of the FGF-7 has comparable homology with the distal two thirds of the other members of the group. See Miyamoto (1993) at page 4254 (FIG. 2).

FGF-8:The cDNA and deduced amino acid sequence of mFGRF-8 is well-known in the art and disclosed in Tanaka et. A., "Cloning and Characterization of an Androgen-Induced Growth Factor Essential for the Growth of Mouse Mammary Caricnoma Cells," PNAS USA, 89:8928-8932 (1992) at FIG. 2. Tanaka also discloses a method for making recombinant FGF-8. The mFGF-8 of Tanaka has 215 amino acid residues. MacArthur, et al., "FGF-8 isoforms activate receptor splice forms that are expressed in mesenchymal regions of mouse development," Development, 1212:3603-3613 (1995) discloses the FGF-8 has 8 different insoforms that differ at the mature N-terminus but that are identical over the C-terminal region. The 8 isoforms arise because FGF-8 has 6 exons of which the first four (which correspond to the first exon of most other FGF genes) result in alternative splicing.

FGF-9:The cDNA and deduced amino acid sequences of human and murine FGF-9 are known in the art and methods for their recombinant expressions are disclosed in Santos-Ocamp, et. Al., "Expression and Biological Activity of Mouse Fibroblast Growth Factor," J. Biol. Chem., 271(3): 1726-1731 (1996). Both the human and murine FGF-9 molecules have 208 amino acid residues and sequences that differ by only two residues. In particular, HFGF-9 has Ser and Asn at residues 9 and 34, respectively. FGF-9 has complete preservation of the conserved amino acids that define the FGF family. Santos-Ocamp (1996) at page 1726. Half-maximal activation of FGf-9 is seen at 185 ng/ml heparin, whereas half-maximal activation of FGF-1 is seen at 670 ng/ml heparin. Santos-Ocampo (1996) at page 1730. When compared to FGF-1, both FGF-1, both FGF-2 and FGF-9 require lower heparin concentrations for optimal activity.

FGF-98:The cDNA and amino acid sequence of hFGF-98 and a method for its recombinant expression are disclosed in provisional patent application Serial No. 60/083,553 which is hereby incorporated herein by reference in its entirety. HFGF-98, which is also known as hFGF-18, has 207 amino acid residues. Thus, hFGF-6 (207 residues), hFGF-9 (208 residues) and hFGF-98 (207 residues) are similar in size.

bFGF-2, and other FGFs, can be made as described in U.S. Pat. No. 5,155,214 ("the '214 patent"). The recombinant bFGF-2, and other FGFs, can be purified to pharmaceutical quality (98% or greater purity) using the techniques described in detail in U.S. Pat. No. 4,956,455 (the '455 patent), entitled "Bovine Fibroblast Growth Factor" which issued on Sep. 11, 1990.

Biologically active variants of FGF are also encompassed by the method of the present invention. Such variants should retain FGF activities, particularly the ability to bind to FGF receptor sites. FGF activity may be measured using standard FGF bioassays, which are known to those of skill in the art. Representative assays include known radioreceptor assays using membranes, a bioassay that measures the ability of the molecule to enhance incorporation of tritiated thymidine, in a dose-dependent manner, into the DNA of cells, and the like. Preferably, the variant has at least the same activity as the native molecule.

In addition to the above described FGFs, the neurologic agent also includes an active fragment of any one of the above-described FGFs. In its simplest form, the active fragment is made by the removal of the N-terminal methionine, using well-known techniques for N-terminal Met removal, such as a treatment with a methionine aminopeptidase. A second desirable truncation includes an FGF without its leader sequence. Those skilled in the art recognize the leader sequence as the series of hydrophobic residues at the N-terminus of a protein that facilitate its passage through a cell membrane but that are not necessary for activity and that are not found on the mature protein.

Preferred truncations on the FGFs are determined relative to mature hFGF-2 (or the analogous bFGF-2) having 146 residues. As a general rule, the amino acid sequence of an FGF is aligned with FGF-2 to obtain maximum homology. Portions of the FGF that extend beyond the corresponding N-terminus of the aligned FGF-2 are generally suitable for deletion without adverse effect. Likewise, portions of the FGF that extend beyond the C-terminus of the aligned FGF-2 are also capable of being deleted without adverse effect.

Fragments of FGF that are smaller than those described can also be employed in the present invention, so long as they retain the cell binding portions of FGF and at least one heparin binding segment. In the case of mature FGF-2 having residues 1-146, the two putative cell binding sites occur at residue positions 36-39 and 77-81 thereof See Yoshida, et al., "Genomic Sequence of hst, a Transforming Gene Encoding a Protein Homologous to Fibroblast Growth Factors and the int-2-Encoded Protein," PNAS USA, 84:7305-7309 (October 1987) at FIG. 3. The two putative heparin binding sites of hFGF-2 occur at residue positions 18-22 and 107-11 thereof. See, Yoshida (1987) at FIG. 3. Accordingly, the active fragments of an FGF typically encompass those terminally truncated fragments of an FGF that when aligned to mature FGF-2 (having residues 1-146) to maximize homology, have at least residues that correspond to residue positions 30-110 of FGF-2; more typically, at least residues that correspond to residues 18-146 of FGF-2.

Suitable biologically active variants can be FGF analogues or derivatives. By "analogue" is intended an analogue of either FGF or an FGF fragment that includes a native FGF sequence and structure having one or more amino acid substitutions, insertions, or deletions. Analogs having one or more peptoid sequences (peptide mimic sequences) are also included (see e.g. International Publication No. WO 91/04282). By "derivative" is intended any suitable modification of FGF, FGF fragments, or their respective analogues, such as glycosylation, phosphorylation, or other addition of foreign moieties, so long as the FGF activity is retained. Methods for making FGF fragments, analogues, and derivatives are available in the art.

In addition to the above-described FGFs, the method of the present invention can also employ an active mutein or variant thereof. By the term active mutein, as used in conjunction with an FGF, is meant a mutated form of the naturally occurring FGF. FGF muteins or variants will generally have at least 70%, preferably 80%, more preferably 85%, even more preferably 90% to 95% or more, and most preferably 98% or more amino acid sequence identity to the amino acid sequence of the reference FGF molecule. A mutein or variant may, for example, differ by as few as 1 to 10 amino acid residues, such as 6-10, as few as 5, as few as 4, 3, 2, or even 1 amino acid residue.

The sequence identity can be determined as described hereinabove. For FGF, a preferred method for determining sequence identify employs the Smith-Waterman homology search algorithm (Meth. Mol. Biol. 70:173-187 (1997)) as implemented in MSPRCH program (Oxford Molecular) using an affine gap search with the following search parameters: gap open penalty of 12, and gap extension penalty of 1. Preferably, the mutations are "conservative amino acid substitutions" using L-amino acids, wherein one amino acid is replaced by another biologically similar amino acid. As previously noted, conservative amino acid substitutions are those that preserve the general charge, hydrophobicity, hydrophilicity, and/or steric bulk of the amino acid being substituted. Examples of conservative substitutions are those between the following groups: Gly/Ala, Val/Ile/Leu, Lys/Arg, Asn/Gln, Glu/Asp, Ser/Cys/Thr, and Phe/Trp/Tyr. In the case of FGF-2, an example of such a conservative amino acid substitution includes the substitution of serine for one or both of the cysteines at residue positions that are not involved in disulfide formation, such as residues 87 and 92 in mature FGF-2 (having residues 1-146).

One skilled in the art, using art known techniques, is able to make one or more point mutations in the DNA encoding any of the FGFs to obtain expression of an FGF polypeptide mutein (or fragment mutein) having angiogenic activity for use in method of the present invention. To prepare an biologically active mutein of an FGF, one uses standard techniques for site directed mutagenesis, as known in the art and/or as taught in Gilman, et al., Gene, 8:81 (1979) or Roberts, et al., Nature, 328:731 (1987), to introduce one or more point mutations into the cDNA that encodes the FGF.

NGF

The term "NGF" as used herein refers to nerve growth factor (NGF). NGF was originally isolated as a complex of molecular weight 130 kDa and a sedimentation coefficient of 7S. This 7S complex included three types of subunits, the "β" subunit carrying all of the biological activities of NGF. The term β-NGF can be used to mean NGF, and the term NGF typically refers to β-NGF. NGF is a dimer of two identical peptide chains each having 118 amino acids and a molecular weight of about 26.5 kDa. Nerve growth factor stimulates mitosis and growth processes associated with cell, particularly nerve cell, development.

In one embodiment of the invention, increasing in the amount of NGF to a therapeutically effective level is achieved via administration of a pharmaceutical composition including a therapeutically effective dose. The NGF to be administered can be from any animal species including, but not limited to, rodent, avian, canine, bovine, porcine, equine, and, preferably, human. Preferably the NGF is from a mammalian species, and more preferably is from a mammal of the same species as the mammal undergoing treatment.

Biologically active variants of NGF are also encompassed by the method of the present invention. Such variants should retain NGF activities, particularly the ability to bind to NGF receptor sites. NGF activity may be measured using standard NGF bioassays, which are known to those of skill in the art. Representative assays include known radioreceptor assays using membranes, a bioassay that measures the ability of the molecule to enhance incorporation of tritiated thymidine, in a dose-dependent manner, into the DNA of cells, and the like. The biological activities of NGF include increasing levels of choline acetyl transferase. Preferably, the variant has at least the same activity as the native molecule.

Suitable biologically active variants can be NGF fragments, analogues, and derivatives. By "NGF fragment" is intended a protein consisting of only a part of the intact NGF sequence and structure, and can be a C-terminal deletion or N-terminal deletion of NGF. By "analogue" is intended an analogue of either NGF or an NGF fragment that includes a native NGF sequence and structure having one or more amino acid substitutions, insertions, or deletions. Analogs having one or more peptoid sequences (peptide mimic sequences) are also included (see e.g. International Publication No. WO 91/04282). By "derivative" is intended any suitable modification of NGF, NGF fragments, or their respective analogues, such as glycosylation, phosphorylation, or other addition of foreign moieties, so long as the NGF activity is retained. Methods for making NGF fragments, analogues, and derivatives are available in the art.

NGF variants will generally have at least 70%, preferably 80%, more preferably 85%, even more preferably 90% to 95% or more, and most preferably 98% or more amino acid sequence identity to the amino acid sequence of the reference NGF molecule. A variant may, for example, differ by as few as 1 to 10 amino acid residues, such as 6-10, as few as 5, as few as 4, 3, 2, or even 1 amino acid residue. Sequence identity and alignment can be determined as described hereinabove.

The art provides substantial guidance regarding the preparation and use of NGF variants. A fragment of NGF will generally include at least about 10 contiguous amino acid residues of the full-length molecule, preferably about 15-25 contiguous amino acid residues of the full-length molecule, and most preferably about 20-50 or more contiguous amino acid residues of full-length NGF.

The NGF used in the present invention can be in its substantially purified, native, recombinantly produced, or chemically synthesized forms. NGF can be isolated and purified from serum, plasma or other tissues by methods known in the art. NGF can also be chemically synthesized by the solid phase method (see Li et al. (1983) *Proc. Natl. Acad. Sci. USA* 80: 2216-2220). This reference is herein incorporated by reference.

Genetic engineering by recombinant DNA techniques can be the most efficient way of producing NGF. The human DNA sequence encoding NGF is known and can be introduced into host cells for expression. NGF can be produced by recombinant DNA techniques in *E. coli*, yeast, insect, and mammalian cells. Secreted NGF can be made by adding a signal sequence to the DNA sequence encoding NGF. In addition, the DNA sequence encoding NGF can be manipulated to make NGF fragments, analogues, or derivatives. Such recombinant DNA techniques are generally available in the art. See, for example, International Publication No. WO 96/07424.

Diagnostic Agents

Diagnostic agents are another preferred category of agent. As used herein, a diagnostic agent is any agent that, when delivered to the CNS, brain, and/or spinal cord, can aid in the diagnosis, detection, localization, monitoring, imaging, or understanding of a disease or disorder in a subject. The disease or disorder need not be of the CNS, brain, and/or spinal cord. The diagnostic agent can be an antibody (preferably a monoclonal antibody), a conjugate, a receptor ligand, an affinity label, a colloidal label, an imaging agent, or the like. Numerous such diagnostic agents are known to those of skill in the art. An antibody diagnostic agent can be labeled with any of a variety of detectable labels employed for detecting antibodies, their complexes, or their conjugates.

For diagnosis of a disease or disorder of the CNS, brain, and/or spinal cord a preferred diagnostic agent can be a polyclonal or monoclonal antibody capable of binding to or detecting a substructure or biochemical marker characteristic of the disease or disorder. Preferably the antibody is monoclonal. Such diagnostic antibodies may be labeled with any labeling agent that may be suitable according to the invention. Suitable labeling agents include, for example, technetium-99m, 123-I, gold or other electron dense particles, positron emitters, and the like. These labels can be detected using appropriate imaging techniques such as single photon emission computed tomography (SPECT), magnetic resonance imaging (MRI), positron emission tomography (PET), computed tomography (CT), and the like, depending upon the type of label used.

The diagnostic agent can also be a chemical reagent that has an affinity for or that can otherwise detect a diseased cell, a pathologic structure or feature, or a biochemical marker (e.g. a receptor). For example, the diagnostic chemical reagent 123-I-quinuclidinyl benzilate (QNB) binds to muscarinic acetylcholine receptors in the brain and may be imaged with SPECT. Another diagnostic chemical reagent, C-nicotine, binds to nicotinic acetylcholine receptors and can be imaged with PET.

Pharmaceutical Composition

Increases in the amount of agent in the CNS, brain, and/or spinal cord to a therapeutically effective level may be obtained via administration of a pharmaceutical composition including a therapeutically effective dose of this agent. By "therapeutically effective dose" is intended a dose of agent that achieves the desired goal of increasing the amount of this agent in a relevant portion of the CNS, brain, and/or spinal cord to a therapeutically effective level enabling a desired biological activity of the agent. Desired biological activities include an increase in protein phosphorylation, particularly of the IGF-I receptor, in response to IGF-I; and an increase in acetylcholine acetyl transferase in response to NGF.

The invention is, in particular, directed to a composition that can be employed for delivery of a agent to the CNS, brain, and/or spinal cord upon administration to the nasal cavity. The composition can include, for example, any pharmaceutically acceptable additive, carrier, or adjuvant that is suitable for administering a agent through the mucosa or epithelium of the nasal cavity. Preferably, the pharmaceutical composition can be employed in diagnosis, prevention, or treatment of a disease, disorder, or injury of the CNS, brain, and/or spinal cord. Preferably, the composition includes a agent in combination with a pharmaceutical carrier, additive, and/or adjuvant that can promote the transfer of the agent within or through the mucosa or epithelium of the nasal cavity, or along or through a neural system. Alternatively, the agent may be combined with substances that may assist in transporting the agent to sites of nerve cell damage. The composition can include one or several agents.

The composition typically contains a pharmaceutically acceptable carrier mixed with the agent and other components in the pharmaceutical composition. By "pharmaceutically acceptable carrier" is intended a carrier that is conventionally used in the art to facilitate the storage, administration, and/or the healing effect of the agent. A carrier may also reduce any undesirable side effects of the agent. A suitable carrier should be stable, i.e., incapable of reacting with other ingredients in the formulation. It should not produce significant local or systemic adverse effect in recipients at the dosages and concentrations employed for treatment. Such carriers are generally known in the art.

Suitable carriers for this invention include those conventionally used for large stable macromolecules such as albumin, gelatin, collagen, polysaccharide, monosaccharides, polyvinylpyrrolidone, polylactic acid, polyglycolic acid, polymeric amino acids, fixed oils, ethyl oleate, liposomes, glucose, sucrose, lactose, mannose, dextrose, dextran, cellulose, mannitol, sorbitol, polyethylene glycol (PEG), and the like.

Water, saline, aqueous dextrose, and glycols are preferred liquid carriers, particularly (when isotonic) for solutions. The carrier can be selected from various oils, including those of petroleum, animal, vegetable or synthetic origin, for example, peanut oil, soybean oil, mineral oil, sesame oil, and the like. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. The compositions can be subjected to conventional pharmaceutical expedients, such as sterilization, and can contain conventional pharmaceutical additives, such as preservatives, stabilizing agents, wetting, or emulsifying agents, salts for adjusting osmotic pressure, buffers, and the like.

Other acceptable components in the composition include, but are not limited to, buffers that enhance isotonicity such as water, saline, phosphate, citrate, succinate, acetic acid, and other organic acids or their salts. Typically, the pharmaceutically acceptable carrier also includes one or more stabilizers, reducing agents, anti-oxidants and/or anti-oxidant chelating agents. The use of buffers, stabilizers, reducing agents, anti-oxidants and chelating agents in the preparation of protein based compositions, particularly pharmaceutical compositions, is well-known in the art. See, Wang et al., "Review of Excipients and pHs for Parenteral Products Used in the United States." J. Parent. Drug Assn., 34(6):452-462 (1980); Wang et al., "Parenteral Formulations of Proteins and Peptides: Stability and Stabilizers," J. Parent. Sci. and Tech., 42:S4-S26 (Supplement 1988); Lachman, et al., "Antioxidants and Chelating Agents as Stabilizers in Liquid Dosage Forms-Part 1," Drug and Cosmetic Industry, 102(1): 36-38, 40 and 146-148 (1968); Akers, M. J., "Antioxidants in Pharmaceutical Products," J. Parent. Sci. and Tech., 36(5):222-228 (1988); and Methods in Enzymology, Vol. XXV, Colowick and Kaplan eds., "Reduction of Disulfide Bonds in Proteins with Dithiothreitol," by Konigsberg, pages 185-188.

Suitable buffers include acetate, adipate, benzoate, citrate, lactate, maleate, phosphate, tartarate, borate, tri(hydroxymethyl aminomethane), succinate, glycine, histidine, the salts of various amino acids, or the like, or combinations thereof. See Wang (1980) at page 455. Suitable salts and isotonicifiers include sodium chloride, dextrose, mannitol, sucrose, trehalose, or the like. Where the carrier is a liquid, it is preferred that the carrier is hypotonic or isotonic with oral, conjunctival or dermal fluids and have a pH within the range of 4.5-8.5. Where the carrier is in powdered form, it is preferred that the carrier is also within an acceptable non-toxic pH range.

Suitable reducing agents, which maintain the reduction of reduced cysteines, include dithiothreitol (DTT also known as Cleland's reagent) or dithioerythritol at 0.01% to 0.1% wt/wt; acetylcysteine or cysteine at 0.1% to 0.5% (pH 2-3); and thioglycerol at 0.1% to 0.5% (pH 3.5 to 7.0) and glutathione. See Akers (1988) at pages 225 to 226. Suitable antioxidants include sodium bisulfite, sodium sulfite, sodium metabisulfite, sodium thiosulfate, sodium formaldehyde sulfoxylate, and ascorbic acid. See Akers (1988) at pages 225. Suitable chelating agents, which chelate trace metals to prevent the trace metal catalyzed oxidation of reduced cysteines, include citrate, tartarate, ethylenediaminetetraacetic acid (EDTA) in its disodium, tetrasodium, and calcium disodium salts, and diethylenetriamine pentaacetic acid (DTPA). See e.g., Wang (1980) at pages 457-458 and 460-461, and Akers (1988) at pages 224-227.

The composition can include one or more preservatives such as phenol, cresol, paraaminobenzoic acid, BDSA, sorbitrate, chlorhexidine, benzalkonium chloride, or the like. Suitable stabilizers include carbohydrates such as threlose or glycerol. The composition can include a stabilizer such as one or more of microcrystalline cellulose, magnesium stearate, mannitol, sucrose to stabilize, for example, the physical form of the composition; and one or more of glycine, arginine, hydrolyzed collagen, or protease inhibitors to stabilize, for example, the chemical structure of the composition. Suitable suspending agents include carboxymethyl cellulose, hydroxypropyl methylcellulose, hyaluronic acid, alginate, chonodroitin sulfate, dextran, maltodextrin, dextran sulfate, or the like. The composition can include an emulsifier such as polysorbate 20, polysorbate 80, pluronic, triolein, soybean oil, lecithins, squalene and squalanes, sorbitan treioleate, or the like. The composition can include an antimicrobial such as phenylethyl alcohol, phenol, cresol, benzalkonim chloride, phenoxyethanol, chlorhexidine, thimerosol, or the like. Suitable thickeners include natural polysaccharides such as mannans, arabinans, alginate, hyaluronic acid, dextrose, or the like; and synthetic ones like the PEG hydrogels of low molecular weight and aforementioned suspending agents.

The composition can include an adjuvant such as cetyl trimethyl ammonium bromide, BDSA, cholate, deoxycholate, polysorbate 20 and 80, fusidic acid, or the like, and in the case of DNA delivery, preferably, a cationic lipid. Suitable sugars include glycerol, threose, glucose, galactose and mannitol, sorbitol. A suitable protein is human serum albumin.

Preferred compositions include one or more of a solubility enhancing additive, preferably a cyclodextrin; a hydrophilic additive, preferably a mono or oligosachharide; an absorption promoting additives, preferably a cholate, a deoxycholate, a fusidic acid, or a chitosan; a cationic surfactant, preferably a cetyl trimethyl ammonium bromide; a viscosity enhancing additive, preferably to promote residence time of the composition at the site of administration, preferably a carboxymethyl cellulose, a maltodextrin, an alginic acid, a hyaluronic acid, or a chondroitin sulfate; or a sustained release matrix, preferably a polyanhydride, a polyorthoester, a hydrogel, a particulate slow release depo system, preferably a polylactide co-glycolides (PLG), a depo foam, a starch microsphere, or a cellulose derived buccal system; a lipid based carrier, preferably an emulsion, a liposome, a niosomes, or a micelles. The composition can include a bilayer destabilizing additive, preferably a phosphatidyl ethanolamine; a fusogenic additive, preferably a cholesterol hemisuccinate.

Other preferred compositions for sublingual administration include employing a bioadhesive to retain the agent sublingually; a spray, paint, or swab applied to the tongue; retaining a slow dissolving pill or lozenge under the tongue; or the like. Administration of agent through the skin can be accomplished by a variety of methods known to those of skill in the art for transdermal delivery, including a transdermal patch, an ointment, an iontophoretic patch or device, and the like. Other preferred methods for transdermal administration include a bioadhesive to retain the agent on or in the skin; a spray, paint, cosmetic, or swab applied to the skin; or the like.

These lists of carriers and additives is by no means complete and a worker skilled in the art can choose excipients from the GRAS (generally regarded as safe) list of chemicals allowed in the pharmaceutical preparations and those that are currently allowed in topical and parenteral formulations.

For the purposes of this invention, the pharmaceutical composition including agent can be formulated in a unit dosage and in a form such as a solution, suspension, or emulsion. The agent may be administered to the nasal cavity as a powder, a granule, a solution, a cream, a spray (e.g., an aerosol), a gel, an ointment, an infusion, an injection, a drop, or sustained release composition, such as a polymer disk. For buccal administration, the compositions can take the form of tablets or lozenges formulated in a conventional manner. For administration to the eye or other external tissues, e.g., mouth and skin, the compositions can be applied to the infected part of the body of the patient as a topical ointment or cream. The compounds can be presented in an ointment, for instance with a water-soluble ointment base, or in a cream, for instance with an oil in water cream base. For conjunctival applications, the neurologic agent can be administered in biodegradable or non-degradable ocular inserts. The drug may be released by matrix erosion or passively through a pore as in ethylene-vinylacetate polymer inserts. For other mucosal administrations such as sublingual, powder discs may be placed under the tongue and active delivery systems may for in situ by slow hydration as in the formulation of liposomes from dried lipid mixtures or pro-liposomes.

Other preferred forms of compositions for administration include a suspension of a particulate, such as an emulsion, a liposome, an insert that releases the agent slowly, and the like. The powder or granular forms of the pharmaceutical composition may be combined with a solution and with a diluting, dispersing or surface-active agent. Additional preferred compositions for administration include a bioadhesive to retain the agent at the site of administration; a spray, paint, or swab applied to the mucosa or epithelium; a slow dissolving pill or lozenge, or the like. The composition can also be in the form of lyophilized powder, which can be converted into solution, suspension, or emulsion before administration. The pharmaceutical composition having agent is preferably sterilized by membrane filtration and is stored in unit-dose or multi-dose containers such as sealed vials or ampoules.

The method for formulating a pharmaceutical composition is generally known in the art. A thorough discussion of formulation and selection of pharmaceutically acceptable carriers, stabilizers, and isomolytes can be found in *Remington's Pharmaceutical Sciences* (18$^{th}$ ed.; Mack Publishing Company, Eaton, Pa., 1990), herein incorporated by reference.

The agent of the present invention can also be formulated in a sustained-release form to prolong the presence of the pharmaceutically active agent in the treated mammal, generally for longer than one day. Many methods of preparation of a sustained-release formulation are known in the art and are disclosed in *Remingion's Pharmaceutical Sciences* (18$^{th}$ ed.; Mack Publishing Company, Eaton, Pa., 1990), herein incorporated by reference.

Generally, the agent can be entrapped in semipermeable matrices of solid hydrophobic polymers. The matrices can be shaped into films or microcapsules. Examples of such matrices include, but are not limited to, polyesters, copolymers of L-glutamic acid and gamma ethyl-L-glutamate (Sidman et al. (1983) *Biopolymers* 22: 547-556), polylactides (U.S. Pat. No. 3,773,919 and EP 58,481), polylactate polyglycolate (PLGA) such as polylactide-co-glycolide (see, for example, U.S. Pat. Nos. 4,767,628 and 5,654,008), hydrogels (see, for example, Langer et al. (1981) *J. Biomed. Mater. Res.* 15: 167-277; Langer (1982) *Chem. Tech.* 12: 98-105), non-degradable ethylene-vinyl acetate (e.g. ethylene vinyl acetate disks and poly(ethylene-co-vinyl acetate)), degradable lactic acid-glycolic acid copolyers such as the Lupron Depot™, poly-D-(–)-3-hydroxybutyric acid (EP 133,988), hyaluronic acid gels (see, for example, U.S. Pat. No. 4,636,524), alginic acid suspensions, and the like.

Suitable microcapsules can also include hydroxymethylcellulose or gelatin-microcapsules and polymethyl methacrylate microcapsules prepared by coacervation techniques or by interfacial polymerization. See the copending application entitled "*Method for Producing Sustained-release Formulations,*" U.S. patent application Ser. No. 09/187,780, filed Nov. 6, 1998, wherein a agent is encapsulated in PLGA microspheres, herein incorporated by reference. In addition, microemulsions or colloidal drug delivery systems such as liposomes and albumin microspheres, may also be used. See *Remington's Pharmaceutical Sciences* (18$^{th}$ ed.; Mack Publishing Company Co., Eaton, Pa., 1990). Other preferred sustained release compositions employ a bioadhesive to retain the agent at the site of administration.

Among the optional substances that may be combined with the agent in the pharmaceutical composition are lipophilic substances that can enhance absorption of the agent through the mucosa or epithelium of the nasal cavity, or along a neural, lymphatic, or perivascular pathway to damaged nerve cells in the CNS. The agent may be mixed with a lipophilic adjuvant alone or in combination with a carrier, or may be combined with one or several types of micelle or liposome substances. Among the preferred lipophilic substances are cationic liposomes included of one or more of the following: phosphatidyl choline, lipofectin, DOTAP, a lipid-peptoid conjugate, a synthetic phospholipid such as phosphatidyl lysine, or the like. These liposomes may include other lipophilic substances such as gangliosides and phosphatidylserine (PS). Also preferred are micellar additives such as GM-1 gangliosides and phosphatidylserine (PS), which may be combined with the agent either alone or in combination. GM-1 ganglioside can be included at 1-10 mole percent in any liposomal compositions or in higher amounts in micellar structures. Protein agents can be either encapsulated in particulate structures or incorporated as part of the hydrophobic portion of the structure depending on the hydrophobicity of the active agent.

One preferred liposomal formulation employs Depofoam. A agent can be encapsulated in multivesicular liposomes, as disclosed in the copending application entitled "*High and Low Load Formulations of IGF-I in Multivesicular Liposomes,*" U.S. patent application Ser. No. 08/925,531, filed Sep. 8, 1997, herein incorporated by reference. The mean residence time of agent at the site of administration can be prolonged with a Depofoam composition.

When the agent is an FGF and the pharmaceutically acceptable carrier is a liquid carrier, a typical pharmaceutical composition can include about 50 to about 10,000 ng/ml, more typically about 50 to 1500 ng/ml, of an FGF or an active fragment or mutein thereof, 10 mM thioglycerol, 135 mM NaCl, 10 mM sodium citrate, and lmM EDTA, pH 5. A suitable diluent or flushing agent for the above-described composition is any of the above-described carriers. Typically, the diluent is the carrier solution itself, which in this example includes 10 mM thioglycerol, 135 mM NaCl, 10 mM sodium citrate and 1 mM EDTA, pH 5.

When provided in liquid form, such an FGF, or other agent, composition or unit dose can become unstable when stored for extended periods of time. To maximize stability and shelf life, the pharmaceutical compositions and the unit dose compositions should be stored frozen at −60° C. When thawed, the solution can stable for 6 months at refrigerated conditions. A typical vial of the pharmaceutical composition would include about 1.0 to 100 ml (more typically, about 1.0 to 25 ml; most typically, about 1.0 to 10 ml) of the above described pharmaceutically acceptable carrier containing therein from about 5 ng to about 10,000 ng of FGF, or another agent, or an active fragment or mutein thereof.

When the agent is IGF-I, or another agent, the pharmaceutical composition may additionally include a solubilizing compound. For IGF-I, a preferred solubilizing agent, includes a guanidinium group and that is capable of enhancing the solubility of a agent like IGF-I. Examples of such solubilizing compounds include the amino acid arginine, as well as amino acid analogs of arginine that retain the ability to enhance solubility of a agent at pH 5.5 or greater. Such analogs include, without limitation, dipeptides and tripeptides that contain arginine. By "enhancing the solubility" of a agent is intended increasing the amount of agent that can be dissolved in solution at pH 5.5 or greater in the presence of a guanidinium-containing compound compared to the amount of agent that can be dissolved at pH 5.5 or greater in a solution with the same components but lacking the guanidinium-containing compound. The ability of a guanidinium-containing compound to enhance the solubility of a agent can be determined using methods well known in the art. In general, the concentration of the solubilizing compound present in the composition will be from about 10 mM to about 1 M, and, for example, in the case of the compound arginine, in a concentration range of about 20 mM to about 200 mM, as disclosed in the copending application entitled "Compositions Providing for Increased IGF-I Solubility," U.S. patent application Ser. No. 09/188,051, filed Nov. 6, 1998.

A preferred embodiment of the present composition includes an effective amount of NGF with a pharmaceutically-acceptable liquid carrier containing an appropriate amount of micelles included of GM-1 ganglioside. GM-1 is thought to act synergistically with nerve growth factor (NGF) to protect neurons and promote nerve regeneration and repair. Another preferred embodiment includes an antisense oligonucleotide for treating brain tumors. Another preferred embodiment of the composition include the combination of an effective amount of basic fibroblast growth factor (bFGF) or insulin like growth factor-I (IGF-I) with poly(ethylene-co-vinyl acetate) to provide for controlled release of the agents, for example for the treatment of stroke. Yet another preferred embodiment of the pharmaceutical composition of the invention includes a liposomal preparation of basic fibroblast growth factor, or a plasmid encoding bFGF, combined with cationic liposomes included of phosphatidyl choline or lipofectin, a lipid-peptoid conjugate, or a synthetic phospholipid such as phosphatidyl lysine. A preferred embodiment for sublingual administration of the pharmaceutical composition and designed for controlled release are poly(ethylene-co-vinyl acetate) disks containing insulin-like growth factor-I for Alzheimer's Disease, stroke, or head or spinal cord injury.

Administering the Agent

The neurologic agent is typically administered in a dose sufficient to provide a therapeutically effective level in the portion of the CNS, brain, and/or spinal cord that can benefit from the agent. Certain neurologic agents exhibit biological activity at a concentration in or surrounding a tissue of about $10^{-12}$ M to about $10^{-9}$ M, preferably about $10^{-11}$ M to about $10^{-9}$ M, preferably about $10^{-10}$ M. A few of the most potent neurologic agents (e.g. activity dependent neurologic factor, ADNF) exhibit their biological activity in a range as low as about $10^{-15}$ M. Preferred neurologic agents, such as NGF, IGF-I, and bFGF exhibit biological effects in relevant tissues of the CNS, brain, and/or spinal cord at concentrations of about $10^{-11}$ M to about $10^{-9}$ M.

Such a therapeutically effective dose can deliver neurologic agent to a portion of the CNS, brain, or spinal cord relevant to treating a disease, disorder, or injury of these tissues. For example, delivering a neurologic agent to the olfactory bulbs, the hippocampal formation, and/or the frontal cortex can be beneficial to treating Alzheimer's disease. Similarly, delivering a neurologic agent to the midbrain, including the substantia nigra and locus ceruleus, and/or to the brainstem can be beneficial to treating Parkinson's disease. Movement disorders known as ataxias can benefit from treatment directed at the cerebellum. Stroke or injury can affect most parts of the CNS, brain, and/or spinal cord. The method of the invention can deliver therapeutically effective amounts of a neurologic agent to portions of the brain and CNS including the olfactory bulbs, the hippocampal formation, the frontal cortex, the midbrain, the brainstem, and the spinal cord, which portions are relevant to several diseases or disorders of the CNS, brain, and/or spinal cord.

It is recognized that the total amount of neurologic agent administered as a unit dose to a particular tissue will depend upon the type of pharmaceutical composition being administered, that is whether the composition is in the form of, for example, a solution, a suspension, an emulsion, or a sustained-release formulation. For example, where the pharmaceutical composition comprising a therapeutically effective amount of neurologic agent is a sustained-release formulation, neurologic agent is administered at a higher concentration.

It should be apparent to a person skilled in the art that variations may be acceptable with respect to the therapeutically effective dose and frequency of the administration of neurologic agent in this embodiment of the invention. The amount of the neurologic agent administered will be inversely correlated with the frequency of administration. Hence, an increase in the concentration of neurologic agent in a single administered dose, or an increase in the mean residence time in the case of a sustained release form of neurologic agent, generally will be coupled with a decrease in the frequency of administration.

It is appreciated by those of skill in the art that the actual dose of the neurologic agent will depend on a variety of factors that may be specific to the subject undergoing dosing. These factors should be taken into consideration when determining the therapeutically effective dose of neurologic agent and frequency of its administration. For example, the effective dose can depend on the species, age, weight, or general health of the subject; the severity of the disease or disorder; the size and location of the portion of the brain in which an effective amount of agent must be achieved; the frequency and duration of dosing; the type of formulation administered; the characteristics, such as lipophilicity, of the agent and composition; the nature of the agent and its receptors, if any; and the like. Generally, a higher dosage is preferred if the disease or disorder is more severe. It is believed that the rate of transport through a neuron may be independent of species and agent.

Some minor degree of experimentation may be required to determine the most effective dose and frequency of dose administration, this being well within the capability of one skilled in the art once apprised of the present disclosure.

Intermittent Dosing

In another embodiment of the invention, the pharmaceutical composition comprising the therapeutically effective dose of agent is administered intermittently. By "intermittent administration" is intended administration of a therapeutically effective dose of agent, followed by a time period of discontinuance, which is then followed by another administration of a therapeutically effective dose, and so forth. Administration of the therapeutically effective dose may be achieved in a continuous manner, as for example with a sustained-release formulation, or it may be achieved according to a desired daily dosage regimen, as for example with one, two, three or more administrations per day. By "time period of discontinuance" is intended a discontinuing of the continuous sustained-released or daily administration of agent. The time period of discontinuance may be longer or shorter than the period of continuous sustained-release or daily administration. During the time period of discontinuance, the agent level in the relevant tissue is substantially below the maximum level obtained during the treatment. The preferred length of the discontinuance period depends on the concentration of the effective dose and the form of agent used. The discontinuance period can be at least 2 days, preferably is at least 4 days, more preferably is at least 1 week and generally does not exceed a period of 4 weeks. When a sustained-release formulation is used, the discontinuance period must be extended to account for the greater residence time of agent at the site of injury. Alternatively, the frequency of administration of the effective dose of the sustained-release formulation can be decreased accordingly. An intermittent schedule of administration of agent can continue until the desired therapeutic effect, and ultimately treatment of the disease or disorder, is achieved.

In yet another embodiment, intermittent administration of the therapeutically effective dose of agent is cyclic. By "cyclic" is intended intermittent administration accompanied by breaks in the administration, with cycles ranging from about 1 month to about 2, 3, 4, 5, or 6 months, more preferably about 3 months to about 6 months. For example, the administration schedule might be intermittent administration of the effective dose of agent, wherein a single short-term dose is given once per week for 4 weeks, followed by a break in intermittent administration for a period of 3 months, followed by intermittent administration by administration of a single short-term dose given once per week for 4 weeks, followed by a break in intermittent administration for a period of 3 months, and so forth. As another example, a single short-term dose may be given once per week for 2 weeks, followed by a break in intermittent administration for a period of 1 month, followed by a single short-term dose given once per week for 2 weeks, followed by a break in intermittent administration for a period of 1 month, and so forth. A cyclic intermittent schedule of administration of agent to subject may continue until the desired therapeutic effect, and ultimately treatment of the disorder or disease, is achieved.

Neuronal Transport

One embodiment of the present method includes administration of the agent to the subject in a manner such that the agent is transported to the CNS, brain, and/or spinal cord along a neural pathway. A neural pathway includes transport within or along a neuron, through or by way of lymphatics running with a neuron, through or by way of a perivascular space of a blood vessel running with a neuron or neural pathway, through or by way of an adventitia of a blood vessel running with a neuron or neural pathway, or through an hemangiolymphatic system. The invention prefers transport of an agent by way of a neural pathway, rather than through the circulatory system, so that agents that are unable to, or only poorly, cross the blood-brain barrier from the bloodstream into the brain can be delivered to the CNS, brain, and/or spinal cord. The agent, once past the blood-brain barrier and in the CNS, can then be delivered to various areas of the brain or spinal cord through lymphatic channels, through a perivascular space, or transport through or along neurons. In one embodiment, the agent preferably accumulates in areas having the greatest density of receptor or binding sites for that agent.

Use of a neural pathway to transport an agent to the brain, spinal cord or other components of the central nervous system obviates the obstacle presented by the blood-brain barrier so that medications like nerve growth factor (NGF), a protein that cannot normally cross that barrier, can be delivered directly to the brain, cerebellum, brain stem or spinal cord. Although the agent that is administered may be absorbed into the bloodstream as well as the neural pathway, the agent preferably provides minimal effects systemically. In addition, the invention can provide for delivery of a more concentrated level of the agent to neural cells since the agent does not become diluted in fluids present in the bloodstream. As such, the invention provides an improved method of for delivering an agent to the CNS, brain, and/or spinal cord. In addition, delivery of a therapeutic agent to the CNS by a neural pathway can reduce systemic delivery and unwanted systemic side effects. This can maintain whether or not the agent crosses the blood-brain barrier.

The Trigeminal Neural Pathway

One embodiment of the present method includes delivery of the agent to the subject in a manner such that the agent is transported into the CNS, brain, and/or spinal cord along a trigeminal neural pathway. Typically, such an embodiment includes administering the agent to tissue innervated by the trigeminal nerve and outside the nasal cavity. The trigeminal neural pathway innervates various tissues of the head and face that are outside the nasal cavity, as described above. In particular, the trigeminal nerve innervates the oral and conjunctival mucosa or epithelium, and the skin of the face. Application of the agent to a tissue innervated by the trigeminal nerve can deliver the agent to damaged neurons or cells of the CNS, brain, and/or spinal cord. Trigeminal neurons innervate these tissues and can provide a direct connection to the CNS, brain, and/or spinal cord due, it is believed, to their role in the common chemical sense including mechanical sensation, thermal sensation and nociception (for example detection of hot spices and of noxious chemicals).

Delivery through the trigeminal neural pathway can employ lymphatics that travel with the trigeminal nerve to the pons and other brain areas and from there into dural lymphatics associated with portions of the CNS, such as the spinal cord. Transport along the trigeminal nerve can also deliver agents to an olfactory bulb. A perivascular pathway and/or a hemangiolymphatic pathway, such as lymphatic channels running within the adventitia of cerebral blood vessels, can provide an additional mechanism for transport of therapeutic agents to the spinal cord from tissue innervated by the trigeminal nerve.

The trigeminal nerve includes large diameter axons, which mediate mechanical sensation, e.g. touch, and small diameter axons, which mediate pain and thermal sensation, both of whose cell bodies are located in the semilunar (or trigeminal) ganglion or the mesencephalic trigeminal nucleus in the midbrain. Certain portions of the trigeminal nerve extend into the oral and conjunctival mucosa and/or epithelium. Other portions of the trigeminal nerve extend into the skin of the face, forehead, upper eyelid, lower eyelid, dorsum of the nose, side of the nose, upper lip, cheek, chin, scalp and teeth. Individual fibers of the trigeminal nerve collect into a large bundle, travel underneath the brain and enter the ventral aspect of the pons. An agent can be administered to the trigeminal nerve, for example, through the oral, lingual, and/or conjunctival mucosa and/or epithelium; or through the skin of the face, forehead, upper eyelid, lower eyelid, dorsum of the nose, side of the nose, upper lip, cheek, chin, scalp and teeth. Such administration can employ extracellular or intracellular (e.g., transneuronal) anterograde and retrograde transport of the agent entering through the trigeminal nerves to the brain and its meninges, to the brain stem, or to the spinal cord. Once the agent is dispensed into or onto tissue innervated by the trigeminal nerve, the agent may transport through the tissue and travel along trigeminal neurons into areas of the CNS including the brain stem, cerebellum, spinal cord, olfactory bulb, and cortical and subcortical structures.

Delivery through the trigeminal neural pathway can employ movement of an agent across skin, mucosa, or epithelium into the trigeminal nerve or into a lymphatic, a blood vessel perivascular space, a blood vessel adventitia, or a blood vessel lymphatic that travels with the trigeminal nerve to the pons and from there into meningeal lymphatics associated with portions of the CNS such as the spinal cord. Blood vessel lymphatics include lymphatic channels that are around the blood vessels on the outside of the blood vessels. This also is referred to as the hemangiolymphatic system. Introduction of an agent into the blood vessel lymphatics does not necessarily introduce the agent into the blood.

Neural Pathways and Transdermal Administration

In one embodiment, the method of the invention can employ delivery by a neural pathway, e.g. a trigeminal neural pathway, after transdermal administration. Upon transdermal administration, delivery via the trigeminal neural pathway may employ movement of an agent through the skin to reach a trigeminal nerve or a perivascular and/or lymphatic channel that travels with the nerve.

For example, the agent can be administered transdermally in a manner that employs extracellular or intracellular (e.g., transneuronal) anterograde and retrograde transport into and along the trigeminal nerves to reach the brain, the brain stem, or the spinal cord. Once the agent is dispensed into or onto skin innervated by the trigeminal nerve, the agent may transport through the skin and travel along trigeminal neurons into areas of the CNS including the brain stem, cerebellum, spinal cord, olfactory bulb, and cortical and subcortical structures. Alternatively, transdermal administration can result in delivery of an agent into a blood vessel perivascular space or a lymphatic that travels with the trigeminal nerve to the pons, olfactory bulb, and other brain areas, and from there into meningeal lymphatics associated with portions of the CNS such as the spinal cord. Transport along the trigeminal nerve may also deliver transdermally administered agents to the olfactory bulb, midbrain, diencephalon, medulla and cerebellum. The ethmoidal branch of the trigeminal nerve enters the cribriform region. A transdermally administered agent can enter the ventral dura of the brain and travel in lymphatic channels within the dura.

In addition, the method of the invention can be carried out in a way that employs a perivascular pathway and/or a hemangiolymphatic pathway, such as a lymphatic channel running within the adventitia of a cerebral blood vessel, to provide an additional mechanism for transport of agent to the spinal cord from the skin. An agent transported by the hemangiolymphatic pathway does not necessarily enter the circulation. Blood vessel lymphatics associated with the circle of Willis as well as blood vessels following the trigeminal nerve can also be involved in the transport of the agent.

Transdermal administration employing a neural pathway can deliver an agent to the brain stem, cerebellum, spinal cord and cortical and subcortical structures. The agent alone may facilitate this movement into the CNS, brain, and/or spinal cord. Alternatively, the carrier or other transfer-promoting factors may assist in the transport of the agent into and along the trigeminal neural pathway. Transdermal administration of a therapeutic agent can bypass the blood-brain barrier through a transport system from the skin to the brain and spinal cord.

Neural Pathways and Sublingual Administration

In another embodiment, the method of the invention can employ delivery by a neural pathway, e.g. a trigeminal neural pathway, after sublingual administration. Upon sublingual administration, delivery via the trigeminal neural pathway may employ movement of an agent from under the tongue and across the lingual epithelium to reach a trigeminal nerve or a perivascular or lymphatic channel that travels with the nerve.

For example, the agent can be administered sublingually in a manner that employs extracellular or intracellular (e.g., transneuronal) anterograde and retrograde transport through the oral mucosa and then into and along the trigeminal nerves to reach the brain, the brain stem, or the spinal cord. Once the agent is administered sublingually, the agent may transport through the oral mucosa by means of the peripheral processes of trigeminal neurons into areas of the CNS including the brain stem, spinal cord and cortical and subcortical structures. Alternatively, sublingual administration can result in delivery of an agent into lymphatics that travel with the trigeminal nerve to the pons and other brain areas and from there into meningeal lymphatics associated with portions of the CNS such as the spinal cord. Transport along the trigeminal nerve may also deliver sublingually administered agents to the olfactory bulbs, midbrain, diencephalon, medulla and cerebellum. The ethmoidal branch of the trigeminal nerve enters the cribriform region. A sublingually administered agent can enter the ventral dura of the brain and travel in lymphatic channels within the dura.

In addition, the method of the invention can be carried out in a way that employs an hemangiolymphatic pathway, such as a lymphatic channel running within the adventitia of a cerebral blood vessel, to provide an additional mechanism for transport of an agent to the spinal cord from the oral submucosa. An agent transported by the hemangiolymphatic pathway does not necessarily enter the circulation. Blood vessel lymphatics associated with the circle of Willis as well as blood vessels following the trigeminal nerve can also be involved in the transport of the agent.

Sublingual administration employing a neural pathway can deliver an agent to the brain stem, cerebellum, spinal cord and cortical and subcortical structures. The agent alone may facilitate this movement into the CNS, brain, and/or spinal cord. Alternatively, the carrier or other transfer-promoting factors may assist in the transport of the agent into and along the trigeminal neural pathway. Sublingual administration of a therapeutic agent can bypass the blood-brain barrier through a transport system from the oral mucosa to the brain and spinal cord.

Neural Pathways and Conjunctival Administration

In another embodiment, the method of the invention can employ delivery by a neural pathway, e.g. a trigeminal neural pathway, after conjunctival administration. Upon conjunctival administration, delivery via the trigeminal neural pathway may employ movement of an agent from the conjunctiva through the conjunctival epithelium to reach the trigeminal nerves or lymphatic channels that travel with the nerve.

For example, the agent can be administered conjunctivally in a manner that employs extracellular or intracellular (e.g., transneuronal) anterograde and retrograde transport through the conjunctival mucosa and then into and along the trigeminal nerves to reach the brain, the brain stem, or the spinal cord Once the agent is administered conjunctivally, the agent may transport through the conjunctival mucosa by means of the peripheral processes of trigeminal neurons into areas of the CNS including the brain stem, spinal cord and cortical and subcortical structures. Alternatively, conjunctival administration can result in delivery of an agent into lymphatics that travel with the trigeminal nerve to the pons and other brain areas and from there into meningeal lymphatics associated with portions of the CNS such as the spinal cord. Transport along the trigeminal nerve may also deliver conjunctivally administered agents to the olfactory bulbs, midbrain, diencephalon, medulla and cerebellum. The ethmoidal branch of the trigeminal nerve enters the cribriform region. A conjunctivally administered agent can enter the ventral dura of the brain and travel in lymphatic channels within the dura.

In addition, the method of the invention can be carried out in a way that employs an hemangiolymphatic pathway, such as a lymphatic channel running within the adventitia of cerebral blood vessel, to provide an additional mechanism for transport of an agent to the spinal cord from the conjunctival submucosa. An agent transported by the hemangiolymphatic pathway does not necessarily enter the circulation. Blood vessel lymphatics associated with the circle of Willis as well as blood vessels following the trigeminal nerve can also be involved in the transport of the agent.

Conjunctival administration employing a neural pathway can deliver an agent to the brain stem, cerebellum, spinal cord and cortical and subcortical structures. The agent alone may facilitate this movement into the CNS, brain, and/or spinal cord. Alternatively, the carrier or other transfer-promoting factors may assist in the transport of the agent into and along the trigeminal neural pathway. Conjunctival administration of a therapeutic agent can bypass the blood-brain barrier through a transport system from the conjunctival mucosa to the brain and spinal cord.

Disorders of the Central Nervous System

The present method can be employed to deliver agents to the brain for diagnosis, treatment or prevention of disorders or diseases of the CNS, brain, and/or spinal cord. These disorders can be neurologic or psychiatric disorders. These disorders or diseases include brain diseases such as Alzheimer's disease, Parkinson's disease, Lewy body dementia, multiple sclerosis, epilepsy, cerebellar ataxia, progressive supranuclear palsy, amyotrophic lateral sclerosis, affective disorders, anxiety disorders, obsessive compulsive disorders, personality disorders, attention deficit disorder, attention deficit hyperactivity disorder, Tourette Syndrome, Tay Sachs, Nieman Pick, and other lipid storage and genetic brain diseases and/or schizophrenia. The method can also be employed in subjects suffering from or at risk for nerve damage from cerebrovascular disorders such as stroke in the brain or spinal cord, from CNS infections including meningitis and HIV, from tumors of the brain and spinal cord, or from a prion disease. The method can also be employed to deliver agents to counter CNS disorders resulting from ordinary aging (e.g., anosmia or loss of the general chemical sense), brain injury, or spinal cord injury.

The present method can be employed to deliver agents to the brain for diagnosis, treatment or prevention of neurodegenerative disorders. Sublingual, conjunctival or transdermal administration of an agent to peripheral nerve cells of the trigeminal and other sensory neural pathways innervating the skin or the conjunctival or oral mucosa, purported entryway for causative agents of brain diseases, can help protect against disease in these nerve cells and regenerate injured nerve cells, thereby forestalling the subsequent spread of disease to susceptible areas of the CNS, brain, and/or spinal cord.

The application of an agent to the sublingual, conjunctival, or facial epithelium can also help prevent the spread of certain CNS, brain, and/or spinal cord disorders by directly treating peripheral cells and neurons that are injured by neurotoxins and other insults. Prophylactic treatment of these outlying nerve cells helps preclude the entrance of disease-causing agents into the CNS, brain, and/or spinal cord. This method of treatment is particularly beneficial in cases of Alzheimer's disease where an environmental factor is suspected of being one of the causative agents of the disease. Application of an agent to the sensory neurons also in part treats or prevents the loss of smell or of the general chemical sense which may be associated with neurodegenerative diseases and ordinary aging.

Treatment of Parkinson's disease may also be an important application of the present delivery method since the trigeminal nerve pathway can deliver neurotrophins and other therapeutic agents from the oral cavity, conjunctiva, or skin to the pons in the brain stem. The principal therapeutic target in the brain for Parkinson's is the substantia nigra which extends forward over the dorsal surface of the basis peduncle from the rostral border of the pons toward the subthalamic nucleus. Other therapeutic target areas are the locus ceruleus which is located in the rostral pons region and the ventral tegmental area which is located dorsomedial to the substantia nigra.

An "effective amount" of agent is an amount sufficient to prevent, treat, reduce and/or ameliorate the symptoms and/or underlying causes of any of the above disorders or diseases. In some instances, an "effective amount" is sufficient to eliminate the symptoms of those diseases and, perhaps, overcome the disease itself. In the context of the present invention, the terms "treat" and "therapy" and the like refer to alleviate, slow the progression, prophylaxis, attenuation or cure of existing disease. Prevent, as used herein, refers to putting off, delaying, slowing, inhibiting, or otherwise stopping, reducing or ameliorating the onset of such brain diseases or disorders. It is preferred that a large enough quantity of the agent be applied in non-toxic levels in order to provide an effective level of activity within the neural system against the disease. The method of the present invention may be used with any mammal. Exemplary mammals include, but are not limited to rats, cats, dogs, horses, cows, sheep, pigs, and more preferably humans.

Articles and Methods of Manufacture

The present invention also includes an article of manufacture providing an agent for administration to the CNS, brain, and/or spinal cord. The article of manufacture can include a vial or other container which contains a composition suitable for the present method together with any carrier, either dried or in liquid form. The article of manufacture further includes instructions in the form of a label on the container and/or in the form of an insert included in a box in which the container is packaged, for the carrying out the method of the invention. The instructions can also be printed on the box in which the vial is packaged. The instructions contain information such as sufficient dosage and administration information so as to allow the subject or a worker in the field to administer the agent. It is anticipated that a worker in the field encompasses any doctor, nurse, technician, spouse, or other caregiver who might administer the agent. The agent can also be self-administered by the subject.

According to the invention, a agent can be used for manufacturing an agent composition or medicament suitable for conjunctival, transdermal, and/or sublingual administration. The invention also relates to methods for manufacturing an agent composition or medicament suitable for conjunctival, transdermal, and/or sublingual administration. For example, a liquid or solid composition can be manufactured in several ways, using conventional techniques. A liquid composition can be manufactured by dissolving an agent in a suitable solvent, such as water, at an appropriate pH, including buffers or other excipients, for example to form a solution described hereinabove.

The present invention may be better understood with reference to the following examples. These examples are intended to be representative of specific embodiments of the invention, and are not intended as limiting the scope of the invention.

EXAMPLES

Example 1

Sublingual Administration of Insulin-like Growth Factor-I to the Central Nervous System (Brain and Spinal Cord)

Introduction

Administering a neurologic agent sublingually is an effective way to deliver this agent to the brain and spinal cord of an animal.

Material and Methods

Male Sprague-Dawley rats, 200-310 grams, were anesthetized with intraperitoneal pentobarbital (40 mg/kg). Drug delivery to the brain and spinal cord was assessed after sublingual administration of 7.4 nmol of $^{125}$I-IGF-I in phosphate buffered saline, pH 7.4. Rats were placed in on their bellies with posterior elevated and mouth lowered. $^{125}$I-IGF-I (7.4 nmol) on a small strip of filter paper was placed under the tongue. Such methods for sublingual administration are known in the art. Purushotham et al. *Am J. Physiol.* 269,G867-G873 (1995). Rats subsequently underwent perfusion-fixation within minutes following the completion of $^{125}$I-IGF-I administration. Perfusion-fixation was performed with 50-100 ml physiologic saline followed by 500 ml of fixative containing 1.25% glutaraldehyde and 1% paraformaldehyde in 0.1 M Sorenson's phosphate buffer, pH 7.4, prior to dissection and $^{125}$I measurement by gamma counting. Areas dissected included selected brain regions as well as the cervical, thoracic and sacral regions of the spinal cord.

Results

Rapid appearance of neurologic agent in the brain and spinal cord was observed by determining radioactivity. The concentration of neurologic agent was higher in the cervical region of the spinal cord than in the thoracic region and higher in the thoracic region than in the lumbar or sacral regions.

High concentrations of neurologic agent were found in the meninges or dura surrounding each of the following: the olfactory bulb, the dorsal and ventral regions of the brain, the trigeminal nerve and the upper cervical spinal cord. The IGF was also found in the olfactory bulb, spinal cord and brain stem. The trigeminal nerve itself, that innervates the tongue, contained high concentrations of neurologic agent.

Conclusions

The results demonstrate that sublingual administration is an effective method of delivery neurologic agents, such as IGF-I, to the brain, trigeminal nerve and spinal cord.

Example 2

Transdermal Administration of Insulin-like Growth Factor-I to the Central Nervous System (Brain and Spinal Cord)

Introduction

Administering a neurologic agent transdermally is an effective way to deliver this agent to the brain and spinal cord of an animal.

Material and Methods

Male Sprague-Dawley rats, 200-310 grams, are anesthetized with intraperitoneal pentobarbital (40 mg/kg). Drug delivery to the brain and spinal cord was assessed after transdermal administration of 7.4 nmol of $^{125}$I-IGF-I in phosphate buffered saline, pH 7.4. Rats are placed in on their bellies with posterior elevated and mouth lowered. $^{125}$I-IGF-I (7.4 nmol) placed on the skin of the rat's face. Rats subsequently underwent perfusion-fixation within minutes following the completion of $^{125}$I-IGF-I administration. Perfusion-fixation was performed with 50-100 ml physiologic saline followed by 500 ml of fixative containing 1.25% glutaraldehyde and 1% paraformaldehyde in 0.1 M Sorenson's phosphate buffer, pH 7.4, prior to dissection and $^{125}$I measurement by gamma counting. Areas dissected included selected brain regions as well as the cervical, thoracic and sacral regions of the spinal cord.

Results

Rapid appearance of neurologic agent in the brain and spinal cord is observed by determining radioactivity.

Conclusions

The results demonstrate that transdermal administration can be an effective method of delivery for neurologic agents, such as IGF-I, to the brain, trigeminal nerve, and spinal cord.

Example 3

Conjunctival Administration of Insulin-like Growth Factor-I to the Central Nervous System (Brain and Spinal Cord)

Introduction

Administering a neurologic agent conjunctivally is an effective way to deliver this agent to the brain and spinal cord of an animal.

Material and Methods

Male Sprague-Dawley rats, 200-310 grams, are anesthetized with intraperitoneal pentobarbital (40 mg/kg). Drug delivery to the brain and spinal cord was assessed after transdermal administration of 7.4 nmol of $^{125}$I-IGF-I in phosphate buffered saline, pH 7.4. Rats are placed in on their bellies with posterior elevated and mouth lowered. $^{125}$I-IGF-I (7.4 nmol) placed on the rat's lower eyelid. Rats subsequently underwent perfusion-fixation within minutes following the completion of $^{125}$I-IGF-I administration. Perfusion-fixation was performed with 50-100 ml physiologic saline followed by 500 ml of fixative containing 1.25% glutaraldehyde and 1% paraformaldehyde in 0.1 M Sorenson's phosphate buffer, pH 7.4, prior to dissection and $^{125}$I measurement by gamma counting. Areas dissected included selected brain regions as well as the cervical, thoracic and sacral regions of the spinal cord.

Results

Rapid appearance of neurologic agent in the brain and spinal cord is observed by determining radioactivity.

Conclusions

The results demonstrate that conjunctival administration can be an effective method of delivery for neurologic agents, such as IGF-I, to the brain, trigeminal nerve, and spinal cord.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds.

All publications and patent applications in this specification are indicative of the level of ordinary skill in the art to which this invention pertains. The present application includes, incorporated by reference, the co-pending, co-owned application filed concurrently with parent U.S. application Ser. No. 09/458,562 entitled "ADMINISTRATION OF NEUROTROPHIC AGENTS TO THE CENTRAL NERVOUS SYSTEM," and assigned U.S. application Ser. No. 09/458,566.

The invention has been described with reference to various specific and preferred embodiments and techniques. However, it should be understood that many variations and modifications may be made while remaining within the spirit and scope of the invention.

What is claimed is:

1. A method for delivering a neurologic agent to the central nervous system of a mammal in need of treatment for a central nervous system disorder, said method comprising transdermally administering a composition comprising said neurologic agent at a region of the skin of a mammal that is innervated by the trigeminal nerve and outside the nasal cavity of the mammal, said neurologic agent selected from the group consisting of a nerve growth factor, and a fibroblast growth factor.

2. The method according to claim 1, wherein the neurologic agent is delivered to a hippocampal formation, an amygdaloid nuclei, a nucleus basalis of Meynert, a locus ceruleus, a brainstem raphe nuclei, or a combination thereof.

3. The method according to claim 1, wherein the neurologic agent is delivered to a spinal cord, a brain stem, a cortical structure, a subcortical structure, or a combination thereof.

4. The method according to claim 1, wherein the neurologic agent is delivered to lymphatics associated with the central nervous system.

5. The method according to claim 1, wherein the neurologic agent is administered to skin on the face, the forehead, an upper eyelid, a lower eyelid, a dorsum of the nose, a side of the nose, an upper lip, a cheek, a chin, a scalp, or a combination thereof.

6. The method according to claim 1, wherein the neurologic agent is a nerve growth factor.

7. The method according to claim 1, wherein the neurologic agent is a fibroblast growth factor.

* * * * *